(12) United States Patent
Ogawa

(10) Patent No.: US 10,625,025 B2
(45) Date of Patent: Apr. 21, 2020

(54) PREFILLED SYRINGE

(71) Applicant: TERUMO KABUSHIKI KAISHA, Tokyo (JP)

(72) Inventor: Junichi Ogawa, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 443 days.

(21) Appl. No.: 15/280,637

(22) Filed: Sep. 29, 2016

(65) Prior Publication Data
US 2017/0014574 A1 Jan. 19, 2017

Related U.S. Application Data

(63) Continuation of application No. PCT/JP2015/056188, filed on Mar. 3, 2015.

(30) Foreign Application Priority Data

Mar. 31, 2014 (JP) ................................. 2014-074958

(51) Int. Cl.
*A61M 5/315* (2006.01)
*A61M 5/50* (2006.01)
(Continued)

(52) U.S. Cl.
CPC ........ *A61M 5/3157* (2013.01); *A61M 5/3137* (2013.01); *A61M 5/46* (2013.01);
(Continued)

(58) Field of Classification Search
CPC .............. A61M 5/3157; A61M 5/3137; A61M 2005/3104; A61M 2005/3159;
(Continued)

(56) References Cited

U.S. PATENT DOCUMENTS 5,380,295 A * 1/1995 Vacca ................... A61M 5/315
604/187
2006/0184136 A1* 8/2006 Kleyman .......... A61M 5/31595
604/210
(Continued)

FOREIGN PATENT DOCUMENTS

JP 2007-159717 A 6/2007
JP 2008-073519 A 4/2008
(Continued)

OTHER PUBLICATIONS

International Search Report issued in International Patent Application No. PCT/JP2015/056188 dated Jun. 2, 2015.

*Primary Examiner* — Rebecca E Eisenberg
*Assistant Examiner* — Tasnim Mehjabin Ahmed
(74) *Attorney, Agent, or Firm* — Foley & Lardner LLP

(57) ABSTRACT

A prefilled syringe includes a syringe barrel including: a liquid drug discharge portion on a distal end of the barrel, and an opening on a proximal end of the barrel; a cap; a gasket located in the syringe barrel; a plunger including: a shaft portion inserted in the syringe barrel from the opening, and a pressing portion located on a proximal end of the shaft portion and configured to be manually pushed by a user, the plunger being movable toward a distal direction by pushing the pressing portion to slide the gasket toward the liquid drug discharge portion; a liquid drug; an upraised portion located on an inner wall of the syringe barrel between the gasket and the opening; and a clicker.

21 Claims, 12 Drawing Sheets

(51) Int. Cl.
  *A61M 5/31* (2006.01)
  *A61M 5/46* (2006.01)
(52) U.S. Cl.
  CPC .............. *A61M 2005/3104* (2013.01); *A61M 2005/3139* (2013.01); *A61M 2005/5033* (2013.01); *A61M 2205/581* (2013.01); *A61M 2205/582* (2013.01); *A61M 2205/586* (2013.01)
(58) Field of Classification Search
  CPC .... A61M 2005/5003; A61M 2205/581; A61M 2205/586; A61M 2205/582
  See application file for complete search history.

(56) References Cited

U.S. PATENT DOCUMENTS

| | | |
|---|---|---|
| 2008/0132852 A1 | 6/2008 | Kleyhan et al. |
| 2009/0105663 A1* | 4/2009 | Brand .................. A61M 5/326 604/197 |
| 2014/0207077 A1 | 7/2014 | Iwase et al. |
| 2015/0190585 A1 | 7/2015 | Iwase et al. |
| 2017/0014573 A1* | 1/2017 | Ogawa ................ A61M 5/3293 |

FOREIGN PATENT DOCUMENTS

| | | |
|---|---|---|
| JP | 2012-139330 A | 7/2012 |
| WO | WO-2013/046855 A1 | 4/2013 |
| WO | WO-2014/045405 A1 | 3/2014 |

\* cited by examiner

D—D

PREFILLED SYRINGE

CROSS-REFERENCE TO RELATED APPLICATIONS

The present application is a bypass continuation of PCT Application No. PCT/JP2015/056188, filed on Mar. 3, 2015, which claims priority to Japanese Application No. 2014-074958, filed on Mar. 31, 2014. Both of these applications are hereby incorporated by reference in their entireties.

BACKGROUND

The present disclosure relates to a prefilled syringe that stores a liquid drug prefilled in its syringe barrel and enables a user to recognize that the liquid drug has completely been discharged.

A prefilled syringe storing a liquid drug in its syringe barrel is used to administer the liquid drug into a subject person, such as a patient, to simplify preparation of the liquid drug for injection and to prevent the liquid drug for injection from being contaminated with bacteria. The prefilled syringe includes a syringe barrel storing a liquid drug. A gasket and a plunger are inserted in the syringe barrel. The gasket seals the syringe barrel in a liquid-tight manner to prevent leakage of the liquid drug, and the plunger slides the gasket. A pressing portion provided at the proximal end of the shaft portion of the plunger is pushed to slide the gasket in the syringe barrel. By the sliding of the gasket, the liquid drug is injected into the body of a subject person through an injection needle attached to the distal end of the syringe barrel.

WO 2013/046855 A discloses a prefilled syringe including a syringe barrel having a tapered liquid drug discharge portion provided on the distal end, an injection needle attached to and communicating with the liquid drug discharge portion, a gasket slidably housed in the syringe barrel, a plunger attached to the proximal surface of the gasket, a liquid drug stored between the gasket and the liquid drug discharge portion in the syringe barrel, an outer tube in which the syringe barrel and the plunger are inserted, a living body contact member that is slidably fit to the distal end of the outer tube and has a sleeve shape to house the injection needle, and a coil spring that urges the living body contact member toward the distal end in the outer tube. The prefilled syringe is used in such a manner that, by pressing the living body contact member onto the surface of a living body, the coil spring is compressed and the living body contact member slides in the outer tube to project the injection needle which then pierces the surface of the living body, such as a skin. Then by separating the living body contact member from the surface of the living body, the coil spring expands to house the injection needle again in the living body contact member.

SUMMARY

Regarding administration of vaccines, such as influenza vaccine, a small dose of intracutaneous administration can effectively stimulate immunity compared to subcutaneous administration. Administration into the intracutaneous tissue, which is stiffer than the subcutaneous tissue, however requires high pressure even for a small dose of administration. The prefilled syringe for intracutaneous administration requires pushing the plunger with a large pushing force compared to the prefilled syringe for subcutaneous administration.

A high pushing force makes it difficult for a user, such as a doctor, who administers a liquid drug into an intracutaneous tissue of a subject person to surely recognize completion of the discharge felt by the gasket abutting the distal end of the inner wall of the syringe barrel. For this reason, the user continues to push the plunger after all the liquid drug has been discharged, which results in a workload of the user of unnecessarily pushing the plunger with a pushing force greater than the pushing load during administration. This increases the workload of doctors, or users, in particular when administering a liquid drug into many subject persons without a break, such as vaccination for a group. The user also feels uneasy because whether all the liquid drug has surely been administered to each subject person is not sure.

Such a problem also arises when using a prefilled syringe configured to administer a highly concentrated liquid drug through an injection needle having small inner and outer diameters to alleviate pain felt by a subject person during piercing with an injection needle and liquid drug administration. Viscosity of biologics, such as insulin, tends to become higher for a higher concentration of the liquid drug. To administer a highly concentrated biologics using a prefilled syringe with a thin injection needle, a plunger should be pushed with a high pushing force compared to a typical prefilled syringe for subcutaneous administration.

A desired prefilled syringe is such that, even for intracutaneous administration of a liquid drug, such as vaccine, or administration of a highly concentrated liquid drug through a thin injection needle which requires a plunger to be pushed with a high pushing force during administration of the liquid drug, completion of administration of the liquid drug can be recognized easily, rapidly, and surely at approximately the same moment so that unnecessarily pushing of the plunger after completion of the discharge of the liquid drug is unnecessary. The present invention is made to solve the aforementioned problem. An object of the present invention is to provide a prefilled syringe that allows a user to recognize easily, rapidly, and surely the completion of the discharge of a liquid drug at approximately the same moment even when the plunger is pushed with a high pushing force during administration of the liquid drug.

The present invention is made to achieve the object and provides a prefilled syringe including: a syringe barrel having a liquid drug discharge portion on a distal end of the barrel and an opening on a proximal end of the barrel; a cap detachably attached to the syringe barrel to seal the liquid drug discharge portion; a gasket inserted in the syringe barrel; a plunger including a shaft portion inserted in the syringe barrel from the opening and a pressing portion provided on a proximal end of the shaft portion to be manually pushed by a user, the plunger being moved toward a distal direction by pushing the pressing portion to slide the gasket toward the liquid drug discharge portion; and a liquid drug stored between the liquid drug discharge portion and the gasket in the syringe barrel and discharged from the liquid drug discharge portion by sliding of the gasket, the prefilled syringe comprising: an upraised portion provided on an inner wall of the syringe barrel between the gasket and the opening and including a step protruding approximately perpendicular to a central axis of the syringe barrel; and a clicker protruding from a side surface of the shaft portion and configured to slide against the upraised portion along with a movement of the plunger toward the distal direction and flex inward in a direction approximately perpendicular to a central axis of the shaft portion by sliding up the upraised portion, the clicker being flipped by crossing over the upraised portion to generate a clicking sound and/or a clicking vibration at approximately a same moment as when the liquid drug is completely discharged.

The prefilled syringe preferably has the height of the step of at least 0.5 mm.

The prefilled syringe may have a difference between M and L such that −3.0 mm≤L−M≤3.0 mm, where M is the advancement distance which the plunger moves until the clicker crosses over the upraised portion and L is the slide distance which the gasket slides until the liquid drug has completely been discharged.

The prefilled syringe is preferably configured that the clicker includes: a flexing portion branching off from the side surface of the shaft portion and having a inclined section inclined away from the central axis of the shaft portion in a natural state; and a sliding portion connected to the flexing portion and configured to slide against the upraised portion.

The prefilled syringe may be configured that sliding portion includes a sliding portion step provided at a proximal end of the sliding portion to be approximately perpendicular to the central axis of the shaft portion.

The prefilled syringe is preferably configured that the flexing portion includes a distal flexing portion that branches off from a side surface of the shaft portion at distal of the sliding portion to extend toward the sliding portion, the distal flexing portion including the inclined section.

The prefilled syringe is preferably configured that the flexing portion further includes a proximal flexing portion that branches off from a side surface of the shaft portion at proximal of where the distal flexing portion branches off from the side surface of the shaft portion, the proximal flexing portion being connected to the sliding portion and including the inclined section.

The prefilled syringe may be configured that the proximal flexing portion branches off from the side surface of the shaft portion at proximal of the sliding portion.

The prefilled syringe is preferably configured that the flexing portion includes a plurality of arched sections between a first end of the flexing portion connected to the side surface of the shaft portion and a second end of the flexing portion connected to the sliding portion, each of the plurality of arched sections having a curved and/or bent shape, at least a portion of the plurality of the arched sections including the inclined section.

The prefilled syringe is preferably configured that the arched section includes a first arch at the first end of the flexing portion and a second arch at the second end of the flexing portion, the first arch being warped in a convex shape with respect to the side surface of the shaft portion and the second arch being warped in an opposite direction to the first arch.

The prefilled syringe may be configured that the flexing portion includes a distal flexing portion that branches off from the side surface of the shaft portion at distal of the sliding portion to extend toward the sliding portion, the distal flexing portion including the inclined section, and a proximal flexing portion that branches off from the side surface of the shaft portion at proximal of the sliding portion to have an arched section and to be connected to the sliding portion.

The prefilled syringe is preferably configured that the proximal flexing portion is connected to the side surface of the shaft portion at proximal of the sliding portion.

The prefilled syringe may be configured that the distal flexing portion includes a branch-off portion that branches off from the side surface of the shaft portion in a direction perpendicular to the central axis of the shaft portion, and the inclined section that extends from the branch-off portion toward a proximal direction to be connected to the sliding portion and is formed such that a distance from the side surface of the shaft portion gradually increases toward the proximal direction.

The prefilled syringe is preferably configured that the sliding portion includes a slider inclined surface formed such that a distance from the side surface of the shaft portion gradually decreases toward a distal end of the shaft portion.

The prefilled syringe may be configured that the upraised portion includes a slider inclined surface formed such that a distance from the central axis of the syringe barrel gradually decreases toward the distal end of the syringe barrel.

The prefilled syringe is preferably configured that the plunger includes a flange that protrudes from the side surface of the shaft portion to contact the inner wall of the syringe barrel to prevent the plunger from tilting toward the central axis of the syringe barrel.

The prefilled syringe is preferably configured that the flange is provided by at least one at each of distal and proximal of the clicker.

The prefilled syringe is preferably configured that the syringe barrel includes: a syringe barrel body that includes the liquid drug discharge portion on the distal end of the syringe barrel body, and an insertion opening opened at the proximal end of the syringe barrel body, the gasket being disposed inside the syringe barrel body; and an outer tube that has at least a portion extending proximally from a periphery of the insertion opening, the opening provided at the proximal end of the outer tube, and the upraised portion provided at proximal of the insertion opening, an inner diameter of the outer tube from the periphery of the insertion opening to the opening being larger than an inner diameter of the syringe barrel body, wherein the height of the step is smaller than a half of a difference between the inner diameter of the outer tube and the inner diameter of the syringe barrel body.

The prefilled syringe preferably includes a guiding rib or a guiding groove is linearly provided on an inner wall of the outer tube along a central axis of the outer tube, and a guide engaging portion that engages with the guiding rib or the guiding groove to prevent the plunger from rotating and to guide the clicker to the upraised portion is provided on the shaft portion of the plunger.

The prefilled syringe may be configured that the plunger includes an engaging protrusion provided between a portion of the shaft portion to be inserted in the syringe barrel body and the clicker to protrude from the shaft portion, wherein as the plunger is inserted in the outer tube from the opening, the engaging protrusion crosses over the upraised portion and engages with the step to prevent reuse of the prefilled syringe.

The prefilled syringe is preferably configured that the syringe barrel includes the syringe barrel body including a syringe barrel flange protruding from the periphery of the insertion opening and the outer tube in which the syringe barrel body is inserted, the outer tube includes a support protrusion that protrudes from the inner wall of the outer tube to support a distal surface of the syringe barrel flange and a latching claw protruding from the inner wall of the outer tube at a location circumferentially different from the upraised portion, and the syringe barrel flange is immovably held between the support protrusion and the latching claw.

The prefilled syringe may be configured that the plunger is not fixed to the gasket but makes contact with a proximal end of the gasket by a distal end of the plunger to slide the gasket toward the liquid drug discharge portion, and the clicker engages with the step after crossing over the upraised portion to prevent the plunger from returning to an initial position.

The prefilled syringe is preferably used for intracutaneous administration of the liquid drug.

Advantageous Effects of Invention

A prefilled syringe according to the present invention generates a clicking sound and a clicking vibration by flipping a clicker approximately at the same moment as when a liquid drug is completely discharged, so that a user, such as a doctor, can rapidly and surely recognize by a sound or a tactile the completion of the discharge of the liquid drug approximately at the same moment as that. If the plunger is required to be pushed with a high pushing force, a user only has to push the plunger for another few seconds as required after perceiving the clicking sound or the clicking vibration. The user need not worry about whether the liquid drug has completely been administered, and there is no need for a workload of unnecessarily pushing the plunger hard to check that the plunger does not move anymore after completion of the discharge of liquid drug. Since a step approximately perpendicular to the central axis of a syringe barrel is provided at the distal end of an upraised portion, the clicker is surely flipped to generate a clicking sound and a clicking vibration by crossing over the upraised portion. Furthermore, the sliding portion step of the clicker slides against the upraised portion and flexes inward in a direction approximately perpendicular to the central axis of the syringe barrel, so that the timing when the clicking sound and the click feeling are generated almost does not change even when the central axis of a shaft portion of the plunger is deviated from the central axis of the syringe barrel during administration. The user can therefore recognize the completion of the discharge of the liquid drug approximately at the same moment.

DETAILED DESCRIPTION

Embodiments to carry out the present invention will be described below in detail. Note that the scope of the present invention is not limited to the embodiments.

Figure 1:
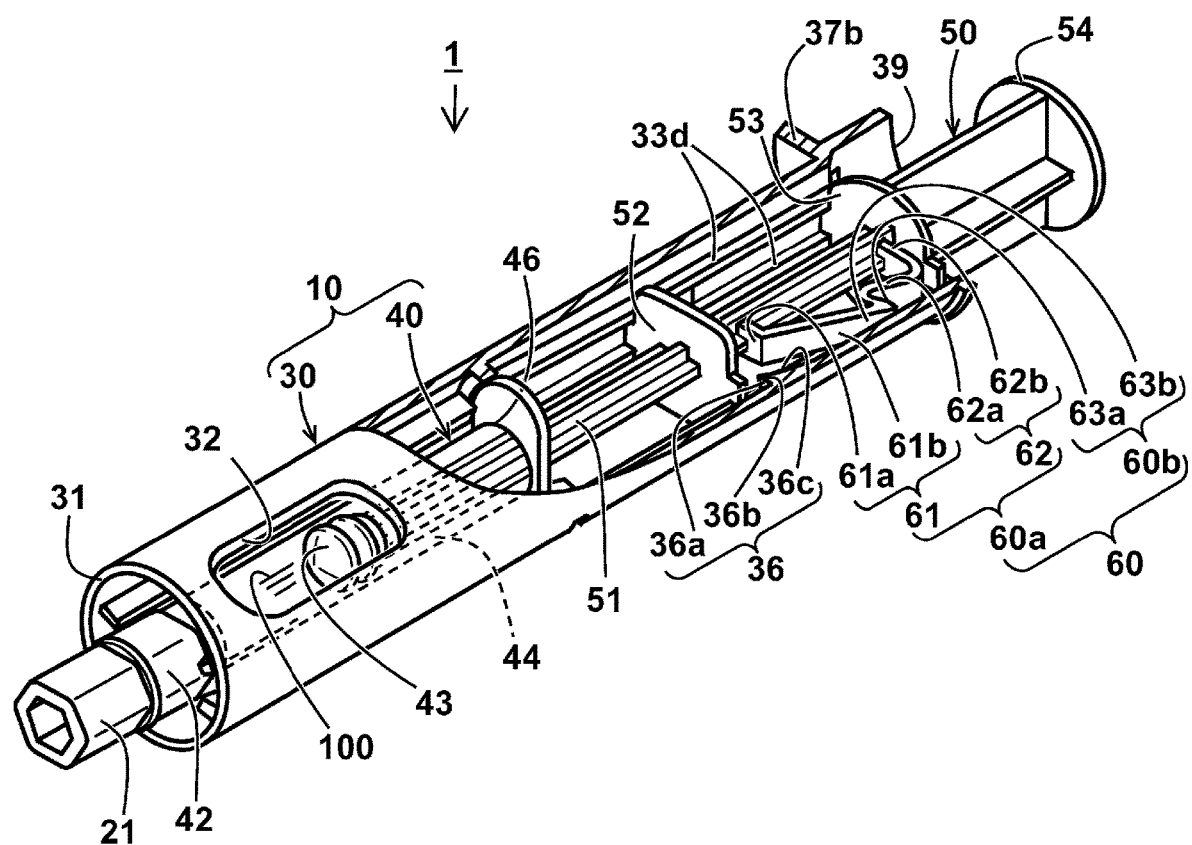
FIG. 1 is a perspective view illustrating, with a portion cut out, one embodiment of a prefilled syringe according to the present invention.

FIG. 1 is a perspective view illustrating, with a portion cut out, one embodiment of a prefilled syringe 1 according to the present invention. The prefilled syringe 1 includes a syringe barrel 10 and a plunger 50. The syringe barrel 10 includes an outer tube 30 and a transparent syringe barrel body 40 storing a liquid drug 100 and inserted in the outer tube 30. The most part of the plunger 50 is inserted in the syringe barrel 10. The outer tube 30, the syringe barrel body 40, and the plunger 50 are coaxially disposed.

The outer tube 30 is a cylinder having opened both ends and an inner diameter larger than the inner diameter of the syringe barrel body 40. An upraised portion 36 is provided at proximal of the insertion opening 46 of the syringe barrel body 40 inserted in the outer tube 30. The upraised portion 36 is provided between a pair of guiding ribs 33d to protrude from the inner wall of the outer tube 30. The upraised portion 36 includes an upraised portion inclined surface 36c, a step 36a, and a top 36b. The distance between the upraised portion inclined surface 36c and the central axis of the outer tube 30 gradually decreases toward a tube distal portion 31 of the outer tube 30. The step 36a approximately vertically rises and the top 36b forms a sharp ridge. The upraised portion inclined surface 36c is slightly curved so that the gradient increases toward the top 36b (see FIG. 2A).

The step 36a may take any form as long as the step is provided from the top 36b, pointing inward, toward the inner wall of the outer tube 30 to be approximately perpendicular to the central axis of the outer tube 30. The surface of the step 36a opposing the distal end need not be approximately perpendicular to the central axis of the outer tube 30 but may have an inclination from the top 36b toward the proximal end.

The outer tube 30 includes an annular protruding portion 37 that is provided near the opening 39 and has a larger outer diameter and a larger inner diameter than those of the tube distal portion 31 (see FIG. 2A), and a brim-shaped finger hooking portion 37b that continues from the annular protruding portion 37 to protrude outward from the outer circumferential surface of the outer tube 30.

The long plunger 50 includes a shaft portion 51 having a crisscross cross section, a clicker 60 protruding from a side surface of the shaft portion 51, flanges 52 and 53 protruding in directions perpendicular to the central axis of the shaft portion 51 as being disposed respectively at distal and proximal of the clicker 60, and a pressing portion 54 that is provided as a disk having a diameter smaller than that of the opening 39 of the outer tube 30 and pushes and moves the plunger 50 toward the tube distal portion 31. The plunger 50 is made of resin. The shaft portion 51, the flanges 52 and 53, the pressing portion 54, and the clicker 60 are integrally formed. A gasket 43 made of elastic material is in contact with the distal end of the plunger 50. The gasket 43 is in liquid-tight contact with the inner wall of the syringe barrel body 40 and can slide inside the syringe barrel body 40. The distal side of the shaft portion 51 is inserted in the syringe barrel body 40.

The clicker 60 branches off from the side surface of the shaft portion 51 to form a thin plate member including a flexing portion 60a that has a inclined section inclined away from the central axis of the shaft portion 51 in a natural state and a sliding portion 60b that is connected to the flexing portion 60a and slides against the upraised portion 36 of the outer tube 30. The flexing portion 60a includes a distal flexing portion 61 branching off from the side surface of the shaft portion 51 at distal of the sliding portion 60b and a proximal flexing portion 62 branching off from the side surface of the shaft portion 51 at proximal of the sliding portion 60b.

The distal flexing portion 61 includes a branch-off portion 61a that branches off from the shaft portion 51 in a direction perpendicular to the central axis of the shaft portion 51 and a distal inclined portion 61b that protrudes from the branch-off portion 61a to extend toward the pressing portion 54 to be connected to the sliding portion 60b. The distal inclined portion 61b is inclined such that the distance from the side surface of the shaft portion 51 gradually decreases from the sliding portion 60b toward the branch-off portion 61a.

The proximal flexing portion 62 includes a joint portion 62b that branches off from the side surface of the shaft portion 51 in a direction perpendicular to the central axis of the shaft portion 51 and an arched section 62a that protrudes from the joint portion 62b to be connected to the sliding portion 60b. The arched section 62a is composed of a first arch having a curved convex shape swelling away from the side surface of the shaft portion 51 and a second arch having a curved shape swelling in the opposite direction to the first arch. A first end of the first arch is connected to the joint portion 62b and a second end is connected to an end of the second arch. The second end of the second arch is connected to the sliding portion 60b. A portion of the arched section 62a serves as the aforementioned inclined section. The inclined section of the flexing portion 60a is composed of the distal inclined portion 61b and a portion of the arched section 62a.

The sliding portion 60b includes a slider inclined surface 63b that continues from the distal inclined portion 61b and slides against the upraised portion inclined surface 36c and a sliding portion step 63a which is a surface provided at the proximal end of the slider inclined surface 63b to be vertical to the central axis of the shaft portion 51. The clicker 60 formed of a thin resin plate has two flexing portions 61 and 62 and thus has high flexibility. The sliding portion step 63a may take any form as long as the step is provided from the top, pointing outward, toward the central axis of the shaft portion 51 to be approximately perpendicular to the central axis of the shaft portion 51. The surface of the sliding portion step 63a opposing the proximal end need not be approximately perpendicular to the central axis of the outer tube 30 but may have an inclination from the top toward the distal end.

Figure 2A:
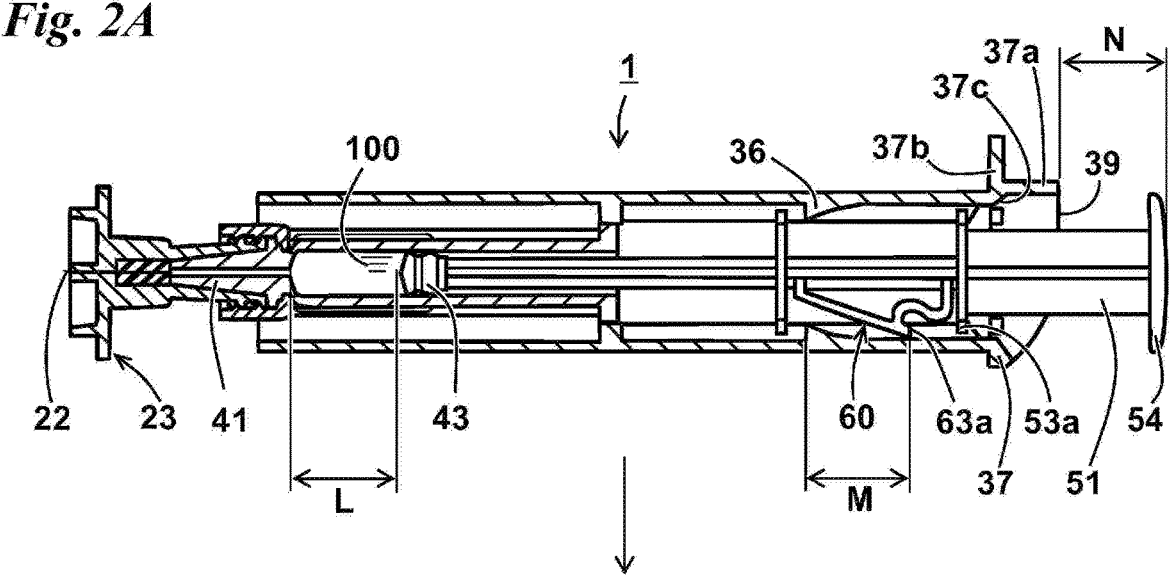
FIGS. 2A to 2C are sectional views illustrating, with a portion cut out, the prefilled syringe according to the present invention being used.

The liquid drug 100 is stored in the internal space of the body portion 44 between the gasket 43 and a liquid drug discharge portion 41 having a smaller diameter than the body portion 44 (see FIG. 2A). A cap 21 for sealing the liquid drug discharge portion 41 is detachably attached by screwing to a luer-lock adaptor 42 provided on the distal end of the syringe barrel body 40. The gasket 43 slides toward the liquid drug discharge portion 41 by a user manually pushing the pressing portion 54 to move the plunger 50 toward the tube distal portion 31. The liquid drug 100 is thereby discharged from the liquid drug discharge portion 41. The plunger 50 is not fixed to the gasket 43. When the plunger 50 moves toward the tube distal portion 31, the distal end of the plunger 50 contacts with the proximal end of the gasket 43 to slide the gasket 43 toward the liquid drug discharge portion 41.

Figure 2B:
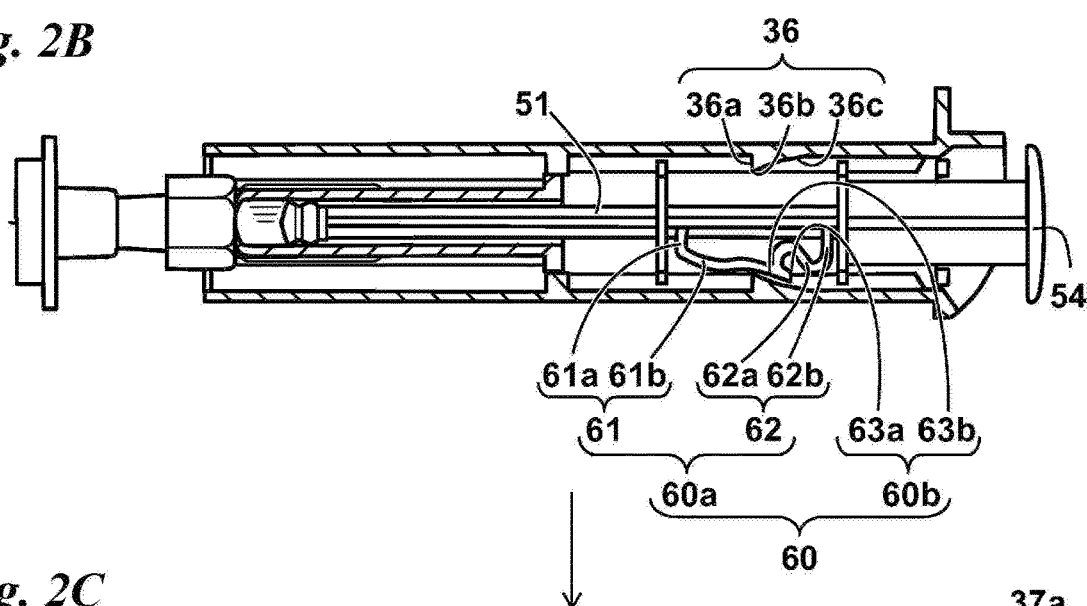
Figure 2C:
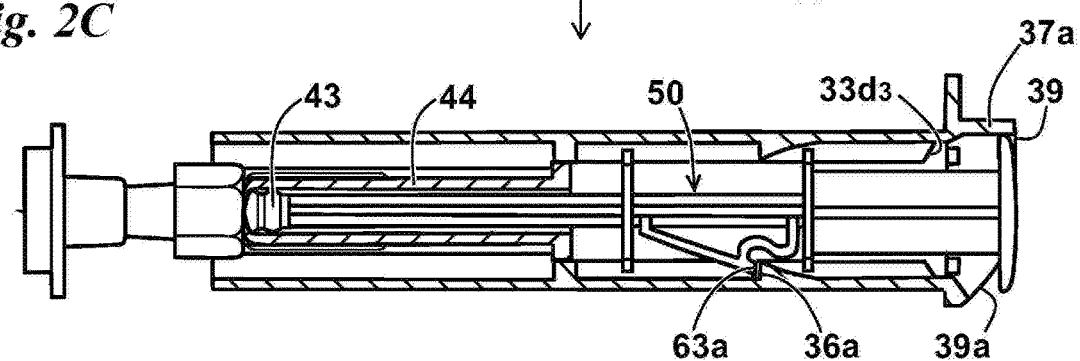

FIGS. 2A to 2C are partial sectional views illustrating the prefilled syringe 1 being used. FIG. 2A illustrates the prefilled syringe 1 just before use where the liquid drug 100 is not yet discharged. Instead of the cap 21, a hub 23 including an injection needle 22 for intracutaneously administering the liquid drug 100 is attached by screwing to the luer-lock adaptor 42 in a manner covering the liquid drug discharge portion 41. The injection needle 22 penetrates the hub 23 and communicates with the internal space of the liquid drug discharge portion 41.

The pressing portion 54 and an identification portion 51a provided between the pressing portion 54 and the flange 53 project from the opening 39. The two upraised portions 36 protrude at locations opposing each other with the central axis of the outer tube 30 therebetween. Slide distance L which the gasket 43 slides to complete the discharge of the liquid drug 100 and the distance between the sliding portion step 63a of the clicker 60 and the top 36b of the upraised portion 36, which is advancement distance M which the plunger 50 moves until the clicker 60 crosses over the upraised portion 36, are approximately equal. Thus, at approximately the same moment as when the gasket 43 reaches the distal end of the body portion 44 to complete the discharge of the liquid drug 100, the clicker 60 crosses over the upraised portion 36.

FIG. 2B illustrates the prefilled syringe 1 discharging the liquid drug 100. FIG. 2B illustrates the pressing portion 54 being pushed to discharge the liquid drug 100 from the injection needle 22. The slider inclined surface 63b of the sliding portion 60b slides against the upraised portion inclined surface 36c of the upraised portion 36 to cause the clicker 60 to slide up the upraised portion 36. The distal inclined portion 61b of the distal flexing portion 61 is slightly flexed to form an S-shape with the branch-off portion 61a and the top 36b being pivot points. The arched section 62a of the proximal flexing portion 62 is flexed, increasing the curvature of each of the first arch and the second arch. The clicker 60, including the flexing portion 60a that has the two sufficiently flexible flexing portions 61 and 62, accumulates therein a high level of stress.

The clicker 60 includes the flexing portion 60a that has an inclined section inclined away from the central axis of the shaft portion 51 in a natural state. This causes, when the flexing portion 60a flexes, the sliding portion 60b to be displaced inward in a direction approximately perpendicular to the central axis of the shaft portion 51. The flexing portion 60a includes a distal flexing portion 61 that branches off from the side surface of the shaft portion 51 at distal of the sliding portion 60b and includes the inclined section, and a proximal flexing portion 62 that branches off from the side surface of the shaft portion 51 at proximal of the sliding portion 60b and includes the inclined section. Thus, along with flexing of the flexing portion 60a, the sliding portion 60b is further surely displaced inward in a direction approximately perpendicular to the central axis of the shaft portion 51 with minimum displacement toward the distal end and the proximal end of the sliding portion 60b.

Along with the flexing of the flexing portion 60a, the proximal flexing portion 62 flexes in a manner increasing the curvature of each of the first arch and the second arch. The stress produced by flexing of the proximal flexing portion 62 is thereby distributed, not concentrated at a local portion, and thus the stress due to the accumulated stress in the clicker 60 is hard to be left as distortion. Thus, by the clicker 60 crossing over the upraised portion 36, the accumulated stress in the clicker 60 is released to surely flip the clicker 60 to vibrate without fail.

The slight curve of the upraised portion inclined surface 36c increasing its gradient toward the top 36b steeply increases the stress as the sliding portion 60b pushed by the pressing portion 54 approaches the top 36b. The stress urges the sliding portion 60b against the upraised portion inclined surface 36c to produce frictional resistance between the sliding portion 60b and the upraised portion inclined surface 36c.

FIG. 2C illustrates the prefilled syringe 1 that has completed discharge of the liquid drug 100. FIG. 2C illustrates the state where the plunger 50 has been fully pushed in and the gasket 43 has reached the distal end of the body portion 44. Approximately at the same moment as when the gasket 43 reaches the distal end, the sliding portion 60b crosses over the top 36b and the stress accumulated in the clicker 60 is instantly released. The clicker 60 is thereby flipped to vibrate, simultaneously generating a clicking sound and a clicking vibration. By perceiving the clicking sound or the clicking vibration, the user can recognize the completion of the discharge of the liquid drug 100. The clicking sound and the clicking vibration also give a person a feeling that the intended operation has been completed. The prefilled syringe 1 can thus give the user a sense of relief that the liquid drug 100 has surely been administered into the subject person.

It is actually difficult for every prefilled syringe 1 to be provided with the same slide distance L of the gasket 43 as the advancement distance M of the plunger 50. So that the distances are preferably provided within the range satisfying the formula: −3.0 mm≤L−M≤3.0 mm. With the slide distance L and the advancement distance M set within such a range, the user can surely administer a specified dose of the liquid drug 100 into a subject person for every prefilled syringe 1 by giving a push for a few seconds to push in the pressing portion 54 of the plunger 50 after perceiving a clicking sound or a clicking vibration. In this manner, the user need not worry whether the liquid drug 100 has surely been administered into the subject person nor be given a workload of unnecessarily continuing a push on the pressing portion 54, with a higher pushing force than a push given to discharge the liquid drug 100, after the plunger 50 has already been fully pushed in.

If the advancement distance M is longer than the slide distance L by more than 3 mm, an unnecessary push on the pressing portion 54 with a higher pushing force than a push given to discharge the liquid drug 100 continues, even after the discharge of the liquid drug 100 has been completed, until the clicker 60 crosses over the upraised portion 36 to generate a clicking sound and a clicking vibration. This increases the workload of the user.

In contrast, if the slide distance L is longer than the advancement distance M by more than 3 mm, a push should be given to the plunger 50 for a longer period of time after generation of the clicking sound and the clicking vibration by the clicker 60 crossing over the upraised portion 36 to completely discharge the liquid drug 100. This might increase the workload of the user or cause the user to stop giving a push to the plunger 50 before completing the discharge of the liquid drug 100, which results in failure of administering a specified dose of the liquid drug 100 into the subject person. The slide distance L and the advancement distance M are preferably set within the range satisfying the formula: −2.5 mm≤L−M≤2.5 mm, more preferably, −2.0≤L−M≤2.0 mm.

As the clicker 60 slides up the upraised portion 36, the clicker 60 flexes inward in the direction approximately perpendicular to the central axis of the shaft portion 51. Specifically, as the clicker 60 slides up the upraised portion 36, the flexing portion 60a having the inclined section inclined away from the central axis of the shaft portion 51 in a natural state flexes, and thereby the sliding portion 60b is displaced inward in the direction approximately perpendicular to the central axis of the shaft portion 51. This configuration provides the prefilled syringe 1, even if the central axis of the shaft portion 51 is deviated from the central axis of the outer tube 30, with little chance of the deviation causing a time gap between the clicking sound and the clicking vibration generated by the clicker 60 and the discharge of the liquid drug 100. Consequently, the clicker 60 can generate the clicking sound and the clicking vibration at the same moment as when the liquid drug 100 is completely discharged independent of the relative movement of the shaft portion 51 of the plunger 50 to the outer tube 30 occurring by pushing the plunger 50 with a high pushing force.

The prefilled syringe 1 generates the clicking sound and the clicking vibration approximately at the same moment as when the liquid drug 100 is completely discharged, so that the user need not worry whether the liquid drug 100 has surely been administered into the subject person nor be given a workload of unnecessarily giving a push on the pressing portion 54, with a higher pushing force than a push given to discharge the liquid drug 100, after the plunger 50 has already been fully pushed in. If the pressing portion 54 is to be pulled back from the opening 39, the sliding portion step 63a abuts the step 36a to prevent the plunger 50 from moving from the position illustrated in FIG. 2C to the position illustrated in FIG. 2A. The clicker 60 thus prevents the prefilled syringe 1 from being mistakenly recognized as unused.

In particular, for a prefilled syringe having the plunger 50 unconnected to the gasket 43 as in the embodiment, the plunger 50 easily returns to the initial position after use, which may cause a user to mistakenly recognize the prefilled syringe 1 as unused. Preventing the return of the plunger 50 by engagement between the clicker 60 (sliding portion step 63a) and the step 36a is effective to be adapted in the prefilled syringe having the plunger 50 unconnected to the gasket 43.

Approximately a half the circumference of the rim of the opening 39 is provided as a concave cutout 39a which is cut in toward the tube distal portion 31. The inner diameter of the opening 39 is slightly larger than the outer diameter of the pressing portion 54. Distance N from the proximal surface of the pressing portion 54 to the opening 39 is approximately the same as the distances L and M, preferably. As illustrated in FIG. 2C, when the liquid drug 100 has completely been discharged, at least a portion of the side surface of the pressing portion 54 and the identification portion 51a are positioned inside the internal space of the proximal extension section 37a.

Near the tube distal portion 31 of the outer tube 30, a square-like inspection hole 32 penetrating the side wall of the outer tube 30 is provided (see FIG. 1). The inspection hole 32 is opened to visually expose the gasket 43 that has reached the distal end of the body portion 44 and the shaft portion 51 in contact with the gasket 43. The prefilled syringe 1 that has completed the discharge of the liquid drug 100 shows the change in external appearance such as the identification portion 51a and the pressing portion 54 being positioned inside the proximal extension section 37a, the gasket 43 reaching the distal end of the body portion 44, and the shaft portion 51 exposed through the inspection hole 32. The user can also recognize by these changes in external appearances the completion of discharge of the liquid drug 100.

The used prefilled syringe 1 that has completely discharged the liquid drug 100 must not be used to pierce another subject person. Exposure of the gasket 43 and the shaft portion 51 through the inspection hole 32 and concealment of the pressing portion 54 inside the proximal extension section 37a attract attention not only of a doctor who actually administers the liquid drug 100 but also of other medical staff, such as nurses, who handles the prefilled syringe 1. Visual checking by more than one personnel who handle the prefilled syringe 1 surely prevents human errors, such as mistakenly piercing another subject person.

When the pressing portion 54 is positioned inside the proximal extension section 37a by completing the discharge of the liquid drug 100, a thumb pushing the pressing portion 54 contacts the cutout 39a. Thus, the user need not change the angle of the thumb just before completing the discharge of the liquid drug 100 to push the pressing portion 54 with the tip of the thumb in order to push in the pressing portion 54 in the internal space of the proximal extension section 37a. As described above, the prefilled syringe 1 not only appeals by the change in the external appearance that the syringe has been used and the liquid drug 100 has completely been discharged but also provides good operability during administration of the liquid drug 100 into the subject person.

The identification portion 51a may have a color different from the pressing portion 54 and the proximal extension section 37a to visually stand out.

The finger hooking portion 37b is held by a finger during administration of the liquid drug 100 and also prevents the prefilled syringe 1 from rolling on and falling off a table, such as a medical table.

Figure 3:
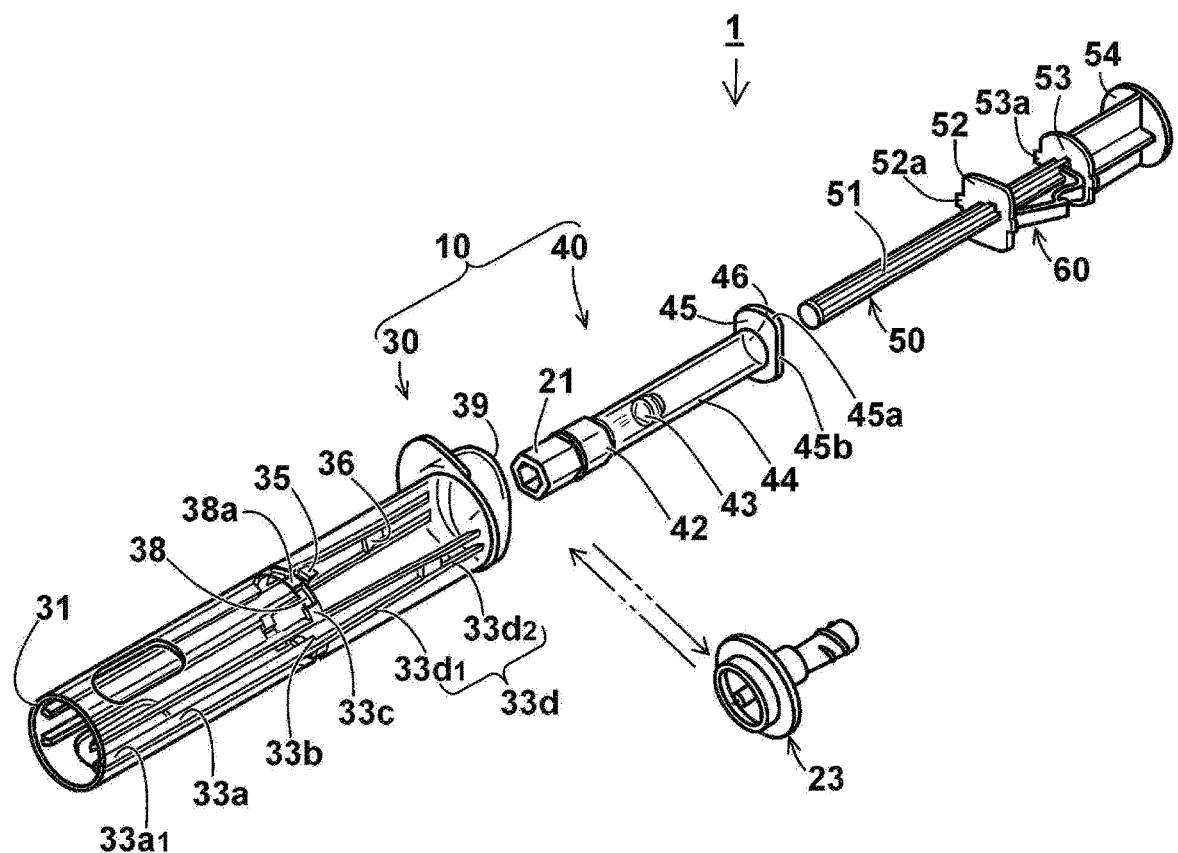
FIG. 3 is an exploded perspective view illustrating one embodiment of the prefilled syringe according to the present invention.

FIG. 3 is an exploded perspective view of the prefilled syringe 1. The syringe barrel body 40 includes the liquid drug discharge portion 41 (see FIG. 2A) provided on the distal end, the luer-lock adaptor 42 surrounding a portion of the side surface of the liquid drug discharge portion 41, the insertion opening 46 provided on the proximal end, a syringe barrel flange 45 protruding radially outward from the rim of the insertion opening 46, and the body portion 44 having an internal space between the liquid drug discharge portion 41 and the insertion opening 46. The syringe barrel flange 45 has a shape with a long axis and a short axis when viewed from the proximal side. The syringe barrel flange 45 has a pair of long-axis side surfaces 45a on both sides in the long axis direction and a pair of short-axis side surfaces 45b on both sides in the short axis direction. Viewed from the proximal side, the outer rim of each of a pair of long-axis side surfaces 45a is an arc formed about the central axis of the syringe barrel body 40. Viewed from the proximal side, the outer rim of each of a pair of short-axis side surfaces 45b is a straight line parallel to the long axis direction. A pair of short-axis side surfaces 45b may be outward convex curved surfaces. The luer-lock adaptor 42 is a sleeve having an external shape of a hexagonal column and an internal thread on the inner wall (see FIG. 2A). The cap 21 with an external thread for sealing the liquid drug discharge portion 41 or the hub 23 are detachably attached by screwing to the luer-lock adaptor 42.

The outer tube 30 is made of a translucent material to allow the internal space to be visible from the external. The outer tube 30 includes the annular protruding portion 37 having a larger diameter than the tube distal portion 31 and the brim-shaped finger hooking portion 37b protruding from the outer circumferential surface of the annular protruding portion 37. The annular protruding portion 37 and the finger hooking portion are provided on the proximal end of the outer tube 30. The finger hooking portion 37b extends in one radial direction approximately perpendicular to the central axis of the outer tube 30. The finger hooking portion 37b thus protrudes perpendicular to the central axis of the outer tube 30. The finger hooking portion 37b is composed of two linear sections tangential to the annular protruding portion 37 and parallel to the protruding direction and an arc section that connects the two linear sections and is concentric to the tube distal portion 31. The finger hooking portion 37b protrudes from the outer circumferential surface of the annular protruding portion 37 in only one radial direction perpendicular to the central axis of the outer tube 30. The user can therefore recognize at a glance that the prefilled syringe is used by holding with the index finger, the middle finger, the fourth finger, and the fifth finger (see FIG. 5).

A pair of protruding linear guiding ribs $33d$ is provided on a proximal portion of the inner wall of the outer tube 30 along the central axis of the outer tube 30. Two pairs of guiding ribs $33d$ are provided at locations opposing each other with the central axis of the outer tube 30 therebetween. A pair of guiding ribs $33d$ includes a pair of proximal guiding ribs $33d_2$ extending from the vicinity of the annular protruding portion 37 to the vicinity of the step 36a of the upraised portion 36 and a pair of distal guiding ribs $33d_1$ extending from the vicinity of the step 36a of the upraised portion 36 toward the tube distal portion 31. The distance between a pair of distal guiding ribs $33d_1$ increases toward the tube distal portion 31.

The syringe barrel body 40 including the liquid drug 100 and the gasket 43 is inserted in the outer tube 30, and then the plunger 50 is inserted in the outer tube 30. The clicker 60 is allowed to slide between a pair of the proximal guiding ribs $33d_2$ with a little play. Thus, as the pressing portion 54 is pushed toward the tube distal portion 31, the clicker 60 is guided toward the upraised portion 36 with the plunger 50 being prevented from rotating. The clicker 60 can thus surely slide against and cross over the upraised portion 36.

The distance between the opposing guiding ribs $33d$ is slightly larger than the width of the portion of the syringe barrel flange 45 that comes between the opposing guiding ribs $33d$ but smaller than the width of the syringe barrel flange 45 along the long axis direction. This allows, during insertion of the syringe barrel body 40 through the opening 39 of the outer tube 30, the short-axis side surface 45b of the syringe barrel flange 45 to be guided by the guiding rib $33d$, and thereby the syringe barrel body 40 is inserted in the outer tube 30 without rotating. The proximal end of the guiding rib 33*d* (proximal guiding rib 33*d*$_2$) reduces its height toward the opening 39, forming a guiding tapered portion 33*d*$_3$ (see FIG. 2C).

On the distal end of a pair of guiding ribs 33*d*, a pair of rotation-restricting ribs 33*c* protrudes from the inner wall of the outer tube 30 so as to oppose the short-axis side surface 45*b* of the syringe barrel flange 45 of the syringe barrel body 40 inserted in the outer tube 30. Likewise a pair of guiding ribs 33*d*, two pairs of rotation-restricting ribs 33*c* are provided at locations opposing each other with the central axis of the outer tube 30 therebetween. Near the distal end of the two pairs of rotation-restricting ribs 33*c*, total four support protrusions 33*b* are provided to protrude toward the central axis of the outer tube 30. The support protrusion 33*b* protrudes further than the rotation-restricting rib 33*c* to hold the syringe barrel flange 45 of the syringe barrel body 40 inserted in the outer tube 30 by the surface of the syringe barrel flange 45 facing the distal end.

Four tilt-restricting ribs 33*a* protrude from the inner wall of the outer tube 30, each continuing from the support protrusion 33*b* to extend to the vicinity of the tube distal portion 31. Adjacent two tilt-restricting ribs 33*a* constitute a pair. Two pairs of tilt-restricting ribs 33*a* are provided at locations opposing each other with the central axis of the outer tube 30 therebetween. The tilt-restricting rib 33*a* is allowed to contact the luer-lock adaptor 42 provided on the distal end of the syringe barrel body 40. This contact restricts tilting of the syringe barrel body 40 toward the outer tube 30 when inserting the syringe barrel body 40 in the outer tube 30. The distal end of the tilt-restricting rib 33*a* is provided as a contact portion 33*a*$_1$ that is allowed to contact the luer-lock adaptor 42 of the syringe barrel body 40 inserted in the outer tube 30.

In the embodiment, the guiding rib 33*d*, the rotation-restricting rib 33*c*, the support protrusion 33*b*, and the tilt-restricting rib 33*a* are continuously provided, and thus as a whole, two pairs of ribs are provided at locations opposing each other with the central axis of the outer tube 30 therebetween. The guiding rib 33*d*, the rotation-restricting rib 33*c*, the support protrusion 33*b*, and the tilt-restricting rib 33*a* may be provided in a non-continuous form.

At a location shifted from the upraised portion 36 by 90 degrees along the circumferential direction of the outer tube 30, a latching claw 35 protrudes from the inner wall of the outer tube 30. Two latching claws 35 are provided at locations opposing each other with the central axis of the outer tube 30 therebetween. The latching claw 35 includes a latching claw inclined surface 35*b* that is inclined such that the distance from the central axis of the outer tube 30 gradually decreases toward the tube distal portion 31 and a latching surface 35*a* that faces the tube distal portion 31 and rises in a direction approximately perpendicular to the central axis of the outer tube 30 (see FIG. 4E). The latching surface 35*a* includes a latching claw protrusion 35*c* protruding toward the tube distal portion 31. To promote elastic deformation of the portion of the outer tube 30 near each latching claw 35 in a radially outward direction, two elastic deformation promoting holes 38 are provided in the outer tube 30 each near the distal end of the latching claw 35. A wobble-restricting rib 38*a* extends from the distal end of each latching claw 35 toward the tube distal portion 31. Each the wobble-restricting rib 38*a* is provided across the elastic deformation promoting hole 38, so that four holes open in the outer tube 30.

When the syringe barrel body 40 is inserted in the outer tube 30, the syringe barrel flange 45 is immovably held between the latching surface 35*a* of the latching claw 35 and the support protrusion 33*b*. Each wobble-restricting rib 38*a* contacts the long-axis side surface 45*a* of the syringe barrel flange 45 to restrict the relative movement of the syringe barrel flange 45 to the outer tube 30 in the long axis direction. The contact portion 33*a*$_1$ contacts the side surface of the luer-lock adaptor 42 to restrict the tilt of the syringe barrel body 40 toward the central axis of the outer tube 30. As described above, the prefilled syringe 1 restricts the movement of the syringe barrel body 40 in the outer tube 30.

The flanges 52 and 53 protrude from the side surface of the shaft portion 51 at locations respectively in the distal side and the proximal side of the clicker 60. That is, the clicker 60 is provided between the flanges 52 and 53. The flanges 52 and 53 contact the inner wall of the outer tube 30 to prevent the shaft portion 51 of the plunger 50 from tilting toward the central axis of the syringe barrel 10 (outer tube 30). This prevents the shaft portion 51 from tilting toward the outer tube 30 even while the pressing portion 54 of the plunger 50 is pushed with a high pushing force. The shaft portion 51 is also supported while the clicker 60 crosses over the upraised portion 36 so as not to flex by the stress produced in the clicker 60 and to tilt toward the syringe barrel 10. The pushing force given to the pressing portion 54 thus acts on the shaft portion 51 along the central axis to smoothly slide the gasket 43. The flange may be provided only one. Preferably, at least one flange is provided in both the distal side and proximal side of the clicker 60. Such a configuration prevents flexing of the shaft portion 51 by the stress produced in the clicker 60 and resulting tilt of the shaft portion 51 toward the syringe barrel 10 which may occur when the clicker 60 crosses over the upraised portion 36.

In the prefilled syringe 1 as described above, the shaft portion 51 of the plunger 50 is supported not to tilt toward the syringe barrel 10 during the discharge of the liquid drug 100. This configuration prevents the timing of completion of the discharge of the liquid drug 100 being different from the timing when the clicking sound or the like is generated, which difference being caused by the tilt of the shaft portion 51 toward the syringe barrel 10. Moreover, the two flanges 52 and 53 support the shaft portion 51 at both sides of the clicker 60, so that the stress accumulated in the clicker 60 does not flex the shaft portion 51. The stress thus does not decline and is accumulated to be used mainly as a force for flipping the clicker 60. So that the trouble of insufficient clicking sound intensity due to insufficient accumulated stress is avoided.

The flanges 52 and 53 engage with the guiding ribs 33*d* to restrict the relative rotation of the plunger 50 to the outer tube 30. This configuration prevents hard contact between the clicker 60 and the proximal guiding rib 33*d*$_2$ caused by the relative rotation of the plunger 50 to the outer tube 30 which might lead to bending or breaking of the clicker 60. During the movement of the plunger 50 toward the tube distal portion 31, the engagement of the flanges 52 and 53 with the guiding ribs 33*d* restricts the relative rotation of the plunger 50 to the outer tube 30 and thereby guides the clicker 60 toward the upraised portion 36. That is, the guiding ribs 33*d* and the flanges 52 and 53 respectively function as guides and guide engaging portions for guiding the clicker 60 toward the upraised portion 36.

The flange 52 includes engaging protrusions 52*a* protruding symmetrically from both sides along the central axis of the shaft portion 51. Each of the engaging protrusions 52*a* is positioned between a pair of guiding ribs 33*d*. As the plunger 50 is inserted in the syringe barrel 10, the engaging protrusion 52*a* of the flange 52 crosses over the upraised portion 36 (see FIG. 1). If the pressing portion 54 is then pulled in a direction away from the opening 39, the engaging protrusion 52a contacts and engages with the step 36a and thereby cannot cross over the upraised portion 36. This prevents contamination caused by unintentionally detaching and dropping the plunger 50 from the outer tube 30 of an unused prefilled syringe 1. As described above, the prefilled syringe 1 has a high level of safety. In particular, for a prefilled syringe including the plunger 50 not connected to the gasket 43 as in the embodiment, engagement between the engaging protrusion 52a and the step 36a is effective to prevent detachment of the plunger 50 from the outer tube 30.

The flange 52 protruding at distal of the clicker 60 has a square-like outer shape. While individually storing and transporting pre-manufactured outer tubes 30 and plungers 50, the plunger 50 may be inserted in the outer tube 30 to be contained with the engaging protrusion 52a and the guiding rib 33d being perpendicular to each other. This prevents bending and breaking of the shaft portion 51 of the plunger 50 during storage and transport. Moreover, the occupying space during storage and transport of pre-manufactured outer tubes 30 and the plungers 50 can be reduced.

Figure 4A:
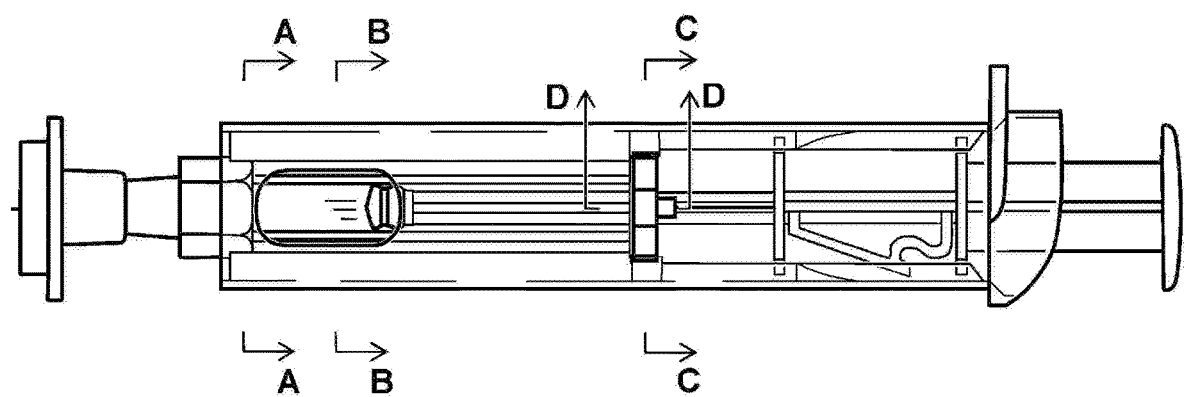
FIG. 4A is a side view of another embodiment of the prefilled syringe according to the present invention.
Figure 4B:
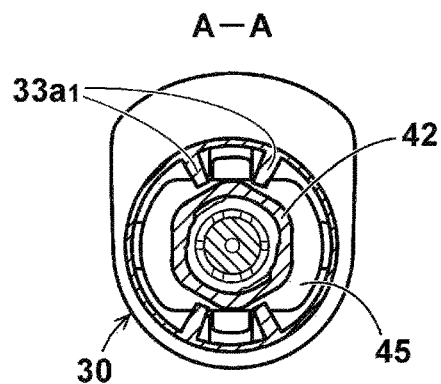
FIG. 4B is a sectional view taken along line A-A in FIG. 4A, illustrating the embodiment of the prefilled syringe according to the present invention.

FIG. 4A is a side view of the prefilled syringe 1. FIG. 4B is a sectional view taken along line A-A in FIG. 4A. The contact portion $33a_1$ provided on the distal end of the tilt-restricting rib 33a opposes the outer circumferential surface of the luer-lock adaptor 42 provided on the distal end of the syringe barrel body 40. The contact portion $33a_1$ protrudes toward the central axis of the outer tube 30. The contact portion $33a_1$ provided on the distal end of the tilt-restricting rib 33a to face the central axis of the outer tube 30 thus contacts the outer circumferential surface of the luer-lock adaptor 42 to surely restrict the tilt of the syringe barrel body 40 toward the central axis of the outer tube 30.

The distance between a pair of tilt-restricting ribs 33a and the distance between two pairs of opposing tilt-restricting ribs 33a are smaller than the outer diameter of the luer-lock adaptor 42. Thus, the contact portion $33a_1$ provided on the distal end of the tilt-restricting rib 33a further surely restricts the tilt of the syringe barrel body 40 toward the central axis of the outer tube 30. The entire wall of the outer tube 30 between the adjacent contact portions $33a_1$ continues without any gap. This prevents the distance between the adjacent contact portions $33a_1$ from widening by the luer-lock adaptor 42 making contact with the contact portion $33a_1$, and thereby the tilt of the syringe barrel body 40 toward the central axis of the outer tube 30 is further surely restricted.

Figure 4C:
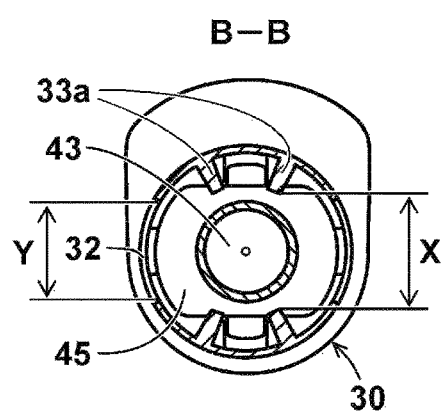
FIG. 4C is a sectional view taken along line B-B in FIG. 4A, illustrating the embodiment of the prefilled syringe according to the present invention.

FIG. 4C illustrates a sectional view taken along line B-B in FIG. 4A. Two inspection holes 32 are provided at locations symmetric about the central axis of the outer tube 30 to open in the direction approximately perpendicular to the direction along which the two sets of tilt-restricting ribs 33a oppose each other. Distance X between the two sets of tilt-restricting ribs 33a opposing each other with the central axis of the outer tube 30 therebetween is larger than width Y of the inspection hole 32 in a cross section perpendicular to the central axis of the outer tube 30. With these dimensions, the tilt-restricting ribs 33a do not interfere in the sight when viewing the inside of the outer tube 30 along the opened direction of the inspection hole 32, allowing the gasket 43, the liquid drug 100, and the shaft portion 51 to be viewed clearly through the inspection hole 32.

Figure 4D:
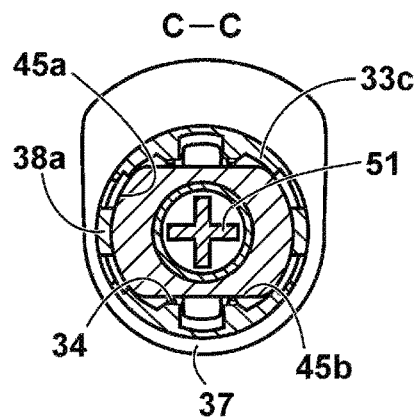
FIG. 4D is a sectional view taken along line C-C in FIG. 4A, illustrating the embodiment of the prefilled syringe according to the present invention.

FIG. 4D illustrates a sectional view taken along line C-C in FIG. 4A. Each pair of rotation-restricting ribs 33c opposes one of a pair of long-axis side surfaces 45a of the syringe barrel flange 45. The distance between the opposing rotation-restricting ribs 33c is approximately identical to the width of the syringe barrel flange 45 that comes between the opposing rotation-restricting ribs 33c but smaller than the width of the syringe barrel flange 45 along the long axis direction. Thus, each of two sets of rotation-restricting ribs 33c contacts the long-axis side surface 45a of the syringe barrel flange 45 to restrict the relative rotation of the syringe barrel body 40 to the outer tube 30 and the movement of the syringe barrel flange 45 in the short axis direction.

A restricting protrusion 34 protrudes from the surface of each rotation-restricting rib 33c opposing the central axis of the outer tube 30. The restricting protrusion 34 is slightly compressingly deformed by the short-axis side surface 45b of the syringe barrel flange 45. This further surely restricts the relative rotation of the syringe barrel body 40 to the outer tube 30 and the movement of the syringe barrel flange 45 in the short axis direction.

The wobble-restricting rib 38a opposes one of a pair of long-axis side surfaces 45a of the syringe barrel flange 45. The distance between the wobble-restricting ribs 38a is approximately identical to the width of the syringe barrel flange 45 along the long axis direction. Thus, each wobble-restricting rib 38a contacts the long-axis side surface 45a of the syringe barrel flange 45 to restrict the relative movement of the syringe barrel flange 45 to the outer tube 30 in the long axis direction.

In this manner, the relative movements to the outer tube 30, in the long axis and the short axis of the syringe barrel flange 45, of the syringe barrel body 40 and the relative rotation of the syringe barrel body 40 to the outer tube 30 are restricted. When viewed along the central axis of the outer tube 30, the shape of the finger hooking portion 37b includes linear sections parallel to the direction in which the finger hooking portion 37b protrudes from the outer wall of the outer tube 30. When inserting the syringe barrel body 40 in the outer tube 30, the direction of the outer tube 30 can be adjusted to the direction of the syringe barrel body 40 using the linear sections and the short-axis side surface 45b of the syringe barrel flanges 45. The side surface of the finger hooking portion 37b includes the arc section connecting the two linear sections by extending along the outer circumference of the outer tube 30. The distance between the two linear sections is approximately identical to the width of the annular protruding portion 37. This allows a parts feeder in the manufacturing line to easily restrict the posture of the outer tube 30.

Figure 4E:
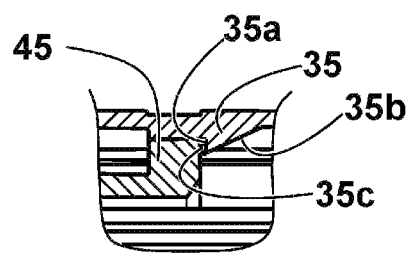
FIG. 4E is a partially enlarged and exploded sectional view taken along line D-D in FIG. 4A, illustrating the embodiment of the prefilled syringe according to the present invention.

FIG. 4E illustrates a partially enlarged view of a section taken along line D-D in FIG. 4A. The latching surface 35a of the latching claw 35 includes a latching claw protrusion 35c protruding toward the tube distal portion 31. The latching claw protrusion 35c is pushed against the proximal side surface of the syringe barrel flange 45 and is slightly compressingly deformed. As a result, there is no play between the latching claw 35 and the syringe barrel flange 45, and thus the syringe barrel body 40 is surely prevented from moving relative to the outer tube 30 in the direction along the central axis of the outer tube 30.

The prefilled syringe 1 is manufactured as described below. The syringe barrel body 40, the luer-lock adaptor 42, and the cap 21 formed by injection molding, for example, are prepared. The luer-lock adaptor 42 is fit on the liquid drug discharge portion 41 so as to surroundingly cover a portion of the side surface of the liquid drug discharge portion 41. The cap 21 is attached by screwing to the luer-lock adaptor 42. The syringe barrel body 40 is suspended in a container (not shown) to be sterilized by high pressure steam, for example.

After sterilization, a liquid drug supply nozzle (not shown) is inserted in the insertion opening 46 of the syringe barrel body 40 to fill the syringe barrel body 40 with the intended liquid drug 100. The gasket 43 is inserted in the syringe barrel body 40 to seal the liquid drug 100 in a liquid-tight manner. This prevents leakage and contamination of the liquid drug 100 in the syringe barrel body 40 while the prefilled syringe 1 is transported or stored.

The outer tube 30 formed by injection molding, for example, is prepared. The outer tube 30 is provided with an inspection hole 32 by pulling out a separable portion of a female die in a direction perpendicular to the axis of the die. The syringe barrel body 40 storing the liquid drug 100 is inserted in the outer tube 30 so as for the short-axis side surface 45$b$ of the syringe barrel flange 45 to oppose the guiding rib 33$d$. In this insertion, the direction of the outer tube 30 can easily be adjusted to the direction of the syringe barrel body 40 using the linear sections of the finger hooking portion 37$b$ and the short-axis side surfaces 45$b$ of the syringe barrel flange 45. The short-axis side surface 45$b$ of the syringe barrel flange 45 is guided by the guiding rib 33$d$ to insert the syringe barrel body 40 into the outer tube 30 without rotating. The guiding tapered portion 33$d_3$ provided at the proximal end of the guiding rib 33$d$ (proximal guiding rib 33$d_2$) allows the syringe barrel flange 45 to be inserted smoothly between the opposing guiding ribs 33$d$.

The syringe barrel body 40 is pushed in until the syringe barrel flange 45 crosses over the latching claw 35 to be immovably held between the support protrusion 33$b$ and the latching claw 35. The syringe barrel body 40 is now engaged in the outer tube 30 and disallowed to come off. Absorbing effect of the elastic deformation promoting holes 38 allows the outer tube 30 to slightly deform radially outward when the syringe barrel flange 45 crosses over the latching claw 35. This deformation allows the syringe barrel flange 45 to cross over the latching claw 35 without compressingly deforming the latching claw 35. The latching claw inclined surface 35$b$ of the latching claw 35 allows the syringe barrel flange 45 to easily cross over the latching claw 35. By the insertion of the syringe barrel body 40 into the outer tube 30 as described above, the syringe barrel body 40 has a portion of the outer tube 30 extending proximally from the periphery of the insertion opening 46.

The plunger 50 including the shaft portion 51, flanges 52 and 53, the pressing portion 54, and the clicker 60 formed by, for example, injection molding is prepared. The plunger 50 is inserted in the syringe barrel 10 from the opening 39 of the outer tube 30 by inserting the shaft portion 51 through the insertion opening 46 of the syringe barrel body 40 so as for the engaging protrusion 52$a$ of the flange 52, the guide engaging portion 53$a$ of the flange 53, and the clicker 60 to be disposed between a pair of guiding ribs 33$d$. During the insertion, the guiding tapered portion 33$d_3$ provided at the proximal end of the guiding rib 33$d$ (proximal guiding rib 33$d_2$) allows the flanges 52 and 53 to be inserted smoothly between the opposing guiding ribs 33$d$. The guiding ribs 33$d$ need not extend as further as to the vicinity of the opening 39 of the outer tube 30 to allow the flange 53 to be inserted between the opposing guiding ribs 33$d$. The plunger 50 is further pushed in until the engaging protrusion 52$a$ crosses over the upraised portion 36, so that the distal surface of the shaft portion 51 of the plunger 50 contacts the proximal surface of the gasket 43. Manufacturing of the prefilled syringe 1 is thus completed.

The prefilled syringe 1 may be configured such that the distal end of the shaft portion 51 of the plunger 50 is not in contact with the proximal end of the gasket 43 before the plunger 50 starts to move toward the tube distal portion 31 by pushing the pressing portion 54. Such a configuration may be achieved, for example, by providing the upraised portion 36 extended to the vicinity of the opening 39 of the outer tube 30 and supporting the sliding portion 60$b$ of the clicker 60 by the upraised portion 36. This configuration prevents movement of the plunger 50 in the syringe barrel 10 while the prefilled syringe 1 is transported or stored.

The provided prefilled syringe 1 is contained in a box-shaped blister packing with a film cover or in a bag packing in an air-tight manner. The prefilled syringe 1 is sterilized in each packing. The hub 23 with the injection needle 22 is manufactured by fixing the injection needle 22 to the hub 23 formed by injection molding or by injection molding the hub 23 together with the injection needle 22. The hub 23 is enclosed by a cover (not shown) to protect the injection needle 22, as required, and is then air tightly contained in a cup-shaped blister packing and sterilized.

The clicker 60 is preferably provided as a thin plate having a thickness ranging from 0.5 mm to 1.5 mm. The clicker 60 thinner than this range breaks by the stress produced by crossing over of the upraised portion 36. With the clicker 60 thicker than this range, a very high pushing force is required to flex the flexing portion 60$a$, which undesirably increases a workload of the user during the discharge of the liquid drug 100.

The height of the step 36$a$ of the upraised portion 36 is preferably at least 0.5 mm. With such a height, a sufficient stress is accumulated in the clicker 60 to surely generate the clicking sound and the clicking vibration by the clicker 60 crossing over the upraised portion 36. The height of the step 36$a$ is preferably smaller than a half of the difference between the inner diameter of the outer tube 30 and the inner diameter of the syringe barrel body 40. Such a height allows the distal end of the plunger 50 to be inserted smoothly in the syringe barrel body 40 without interfering with the upraised portion 36.

A taper 37$c$ that gradually decreases the distance from the central axis of the outer tube 30 toward the tube distal portion 31 is preferably provided on the inner wall of the annular protruding portion 37 (see FIG. 2A). When inserting the plunger 50 in the outer tube 30, the flanges 52 and 53 slide against the taper 37$c$ to be guided to the guiding rib 33$d$ provided further in the distal side than the annular protruding portion 37. The plunger 50 can thus be inserted smoothly in the syringe barrel 10. As illustrated in FIG. 2A, the taper 37$c$ may be provided at an interval or on the full circumference on the inner wall of the annular protruding portion 37. The taper 37$c$ also allows, when inserting the syringe barrel body 40 in the outer tube 30, the syringe barrel flange 45 to be guided smoothly toward the distal end by the annular protruding portion 37. The syringe barrel body 40 can thus be inserted smoothly in the outer tube 30.

Figure 5:
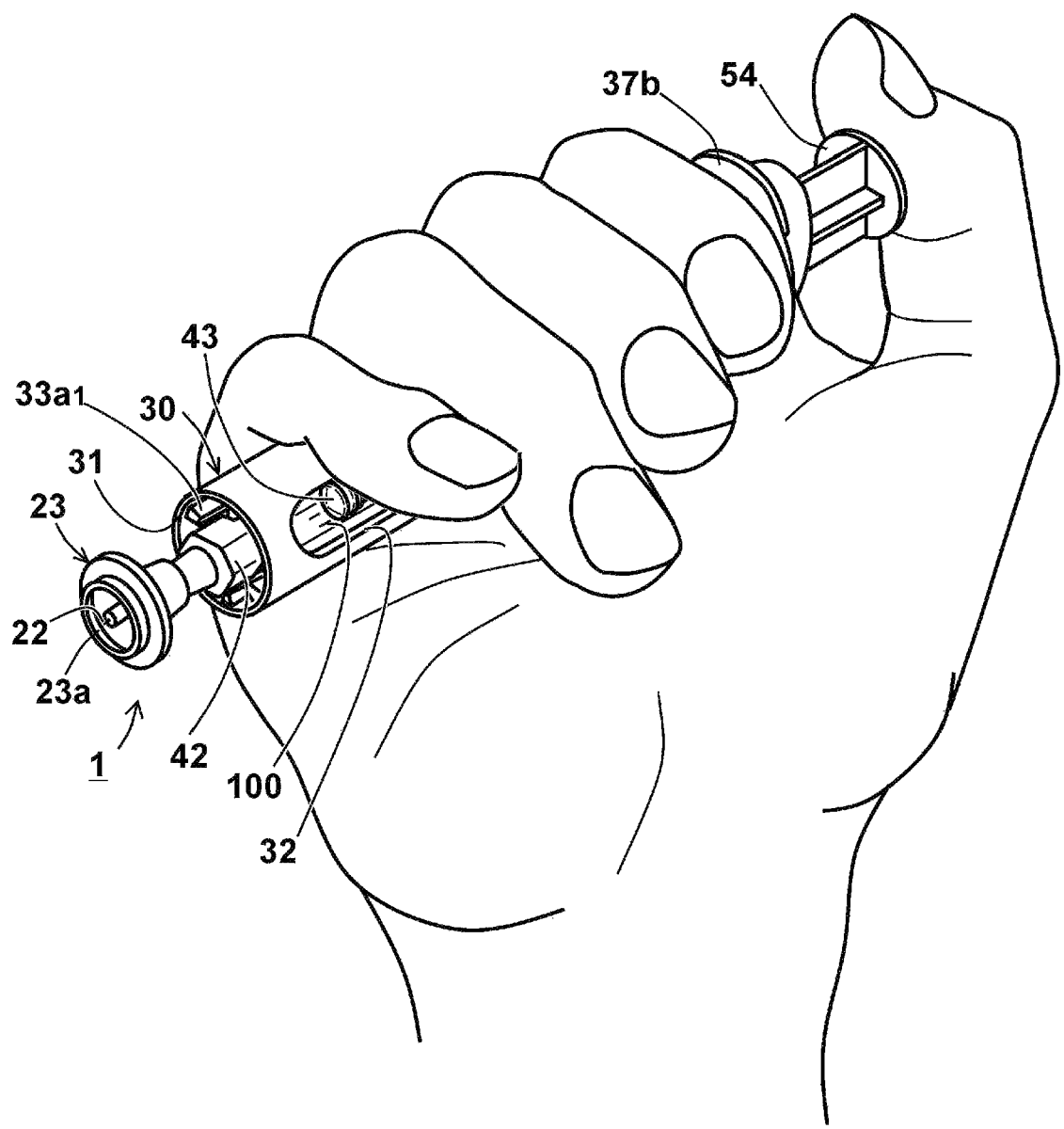
FIG. 5 is a perspective view illustrating how the prefilled syringe according to the present invention is used.

The method of using the prefilled syringe 1 will now be described with reference to FIG. 5. A doctor or a nurse removes the base sheet of a blister packing to take out a prefilled syringe 1 and then removes a cap 21 that has been sealing the liquid drug discharge portion 41. The film cover of the cup-shaped blister packing containing the hub 23 with an injection needle 22 is removed, and then in place of the cap 21, the hub 23 together with the cup-shaped blister packing is attached by screwing to the luer-lock adaptor 42 by screwing. Since the rotation-restricting rib 33$c$ of the outer tube 30 restricts the syringe barrel body 40 from rotating relative to the outer tube 30, the luer-lock adaptor 42 does not rotate together with the hub 23 and can surely be screwed together with the hub 23. A portion of the luer-lock adaptor 42 projects from the tube distal portion 31. The user can thus recognize that the hub 23 is to be attached by screwing.

Since the hub 23 still packed in the cup-shaped blister packing is attached to the liquid drug discharge portion 41, contamination of the injection needle 22 is avoided until immediately before administration of the liquid drug 100. The user can recognize whether the prefilled syringe 1 is unused by visually checking the position of the gasket 43 and the stored liquid drug 100 through the inspection hole 32.

The user then removes the cup-shaped blister packing and holds the outer tube 30 with the thumb on the pressing portion 54, the fifth finger to the hub 23, and the index finger to the finger hooking portion 37b. The annular stabilizer 23a is pressed on a skin of a subject person where injection is to be performed in a manner disallowing swaying of the prefilled syringe 1, and then the annular stabilizer 23a is further firmly pressed on. The injection needle 22 is thereby pierced into the skin of the subject person. For intracutaneous administration of a small dose of the liquid drug 100 such as vaccination, in particular, the injection needle 22 is surely pierced into the skin by pressing the annular stabilizer 23a of the hub 23 on the skin, which avoids leakage of the liquid drug 100 from the distal end of the injection needle 22. The contact portion $33a_1$ of the tilt-restricting rib 33a contacts the outer circumferential surface of the luer-lock adaptor 42 to restrict the tilt of the syringe barrel body 40 toward the central axis of the outer tube 30. In this manner, the injection needle 22 can stably be pierced into the intended portion.

Then, the pressing portion 54 is pushed toward the tube distal portion 31 to move the plunger 50 toward the distal end. With this movement, the gasket 43 pushed by the plunger 50 slides toward the liquid drug discharge portion 41 to discharge the liquid drug 100 from the liquid drug discharge portion 41. The liquid drug 100 discharged from the liquid drug discharge portion 41 is administered through the injection needle 22 of the hub 23 into the subject person. The index finger in contact with the finger hooking portion 37b prevents the fingers holding the outer tube 30 from moving relative to the outer tube 30 further to the proximal side. Therefore, the index finger will not be caught between the opening 39 and the pressing portion 53 and the thumb will not contact the side of the index finger, so that the plunger 50 is fully pushed in to surely intracutaneously inject a specified dose of the liquid drug 100. With the cutout 39a provided in the proximal extension section 37a, the first joint of the thumb has little chance of interfering with the proximal extension section 37a. The user can fully push in the plunger 50 with sureness. Since the contact portion $33a_1$ of the tilt-restricting rib 33a restricts the tilt of the syringe barrel body 40 toward the central axis of the outer tube 30, the liquid drug 100 can stably be administered into the subject person. The liquid drug 100 can stably be administered into the subject person also under a high pushing force required for operating the pressing portion 54. Since the contact portion $33a_1$ of the tilt-restricting rib 33a restricts the tilt of the syringe barrel body 40 toward the central axis of the outer tube 30, the liquid drug 100 can further stably be administered into the subject person. Along with the movement of the plunger 50 toward the distal end, the slider inclined surface 63b slides against the upraised portion inclined surface 36c to accumulate stress in the clicker 60. Approximately at the same moment as when the liquid drug 100 is completely discharged, the clicker 60 crosses over the top 36b of the upraised portion 36 and then the stress accumulated in the clicker 60 is released to flip the clicker 60, generating the clicking sound and the clicking vibration.

The user hears the clicking sound and feels the clicking vibration to recognize that the liquid drug 100 has been discharged from the syringe barrel body 40, completing the administration into the subject person. After perceiving the clicking sound or the clicking vibration, for some cases, the user gives a push for a few seconds to fully push in the pressing portion 54 of the plunger 50 to complete the administration into the subject person.

FIG. 6 is front views of other forms of the clicker 60. As illustrated in FIG. 6A, a pair of clickers 60 of the same shape may protrude from the side surface of the shaft portion 51 to correspond to a pair of upraised portions 36 (see FIGS. 2A to 2C). If a pair of upraised portions 36 and a corresponding pair of clickers 60 are provided, a noise and a vibration larger than a clicking sound or the like generated by a single clicker 60 can be generated. This allows the user to surely hear the clicking sound under noisy circumstances such as in a place where a crowd of people are waiting for protective group vaccination.

Figure 6A:
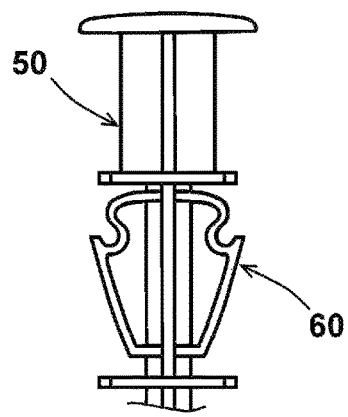
FIGS. 6A to 6D are partial side views of another example of a clicking plate used in the prefilled syringe according to the present invention.
Figure 6B:
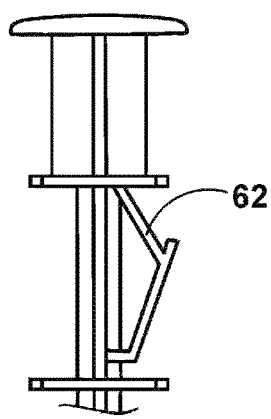

As illustrated in FIG. 6B, if the proximal flexing portion 62 is provided as a plate without an arched section 62a, such a simple shape of the clicker 60 allows the prefilled syringe 1 to be manufactured with low cost.

Figure 6C:
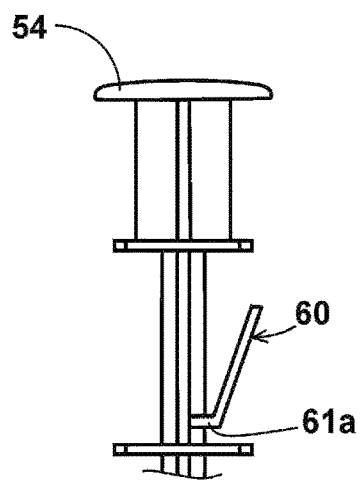

As illustrated in FIG. 6C, the clicker 60 need not include the proximal flexing portion 62. The clicker 60 connected only by the branch-off portion 61a to the side surface of the shaft portion 51 can be flexed by pushing the pressing portion 54 with only a small force. The workload of the user can thus be reduced.

Figure 6D:
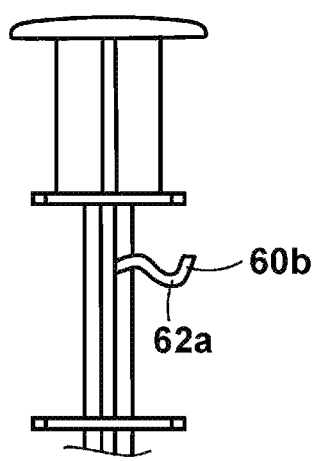

As illustrated in FIG. 6D, the clicker 60 may be composed of the arched section 62a and the sliding portion 60b. The shape of the clicker 60 can be simplified and also the accumulated stress can be distributed to reduce remaining strain in the clicker 60. The shape, material, thickness, hardness, or the like of the clickers 60 illustrated in FIG. 1 and FIGS. 5A to 5D are suitably selected according to the type and the volume of the stored liquid drug 100 and different pushing forces given to the pressing portion 54.

Although an example illustrated in FIG. 3 is provided with symmetrically located two pairs of guiding ribs 33d, a single guiding rib 33d may be linearly provided along the central axis of the outer tube 30. In this case, the guide engaging portion is preferably provided in the flange 52 in a form of a recess to oppose the single guiding rib 33d from both sides. Alternatively, a single guiding groove may be linearly provided along the central axis of the outer tube 30. In this case, the guide engaging portion is provided as a protrusion that protrudes from the shaft portion 51 of the plunger 50 to be inserted in the guiding groove.

Figure 7A:
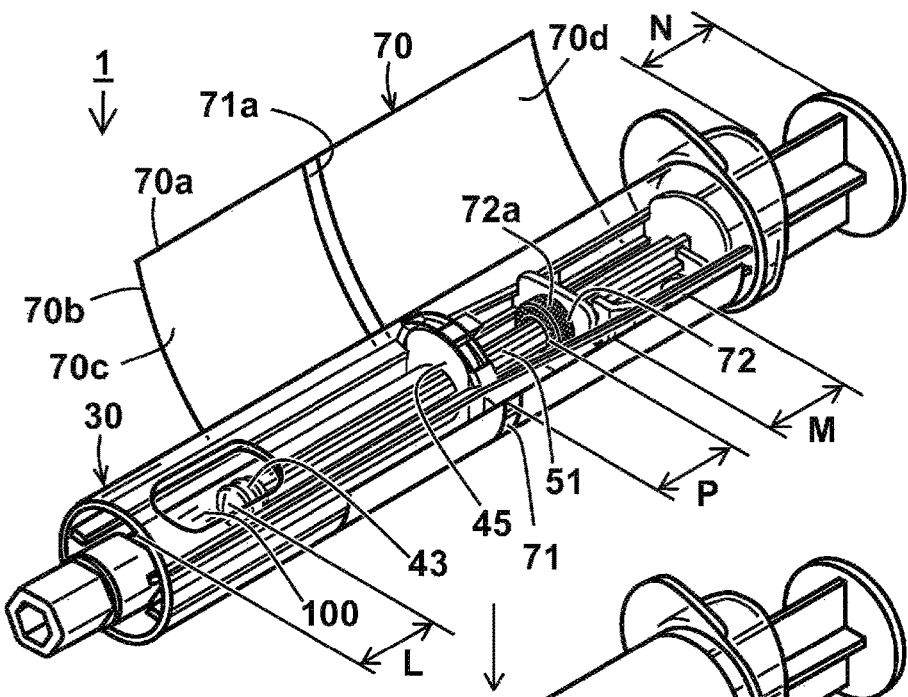
FIGS. 7A to 7C are a partially exploded perspective view of another embodiment of the prefilled syringe and perspective views illustrating the embodiment being used according to the present invention.

FIG. 7A is a partially exploded perspective view illustrating another embodiment of the prefilled syringe 1. FIG. 7A is an illustration with a portion of a label 70 removed from an outer tube 30. The prefilled syringe 1 includes an indicating member 72a provided in the middle of the shaft portion 51. The indicating member 72a is a disk extending outward from the outer circumference of the shaft portion 51. The outer diameter of the indicating member 72a is smaller than the inner diameter of the outer tube 30. The whole surface of the indicating member 72a made of a red resin functions as an indicator 72 to tell medical staff that the prefilled syringe 1 has been used. A hole is provided in the center of the indicating member 72a. The inner diameter of the hole is slightly smaller than the outer diameter of the distal portion of the shaft portion 51 that contacts a gasket 43.

The distal end of the shaft portion 51 is pushed into the hole of the indicating member 72a, thereby slightly expanding the hole to fit the shaft portion 51 in the hole. The indicating member 72a is thus attached to the shaft portion 51. The indicating member 72a made of resin has a little flexibility. So that stress is produced in the indicating member 72a to clamp the shaft portion 51. This stress secures the indicating member 72a to the shaft portion 51. The indicating member 72a may be integrally formed with the plunger 50. In this case, the indicating member 72a may be colored by two-color molding, by painting afterward, or by attaching a label.

A label 70 is wrapped around the outer tube 30 to cover a proximal portion of the outer tube 30 but not around a finger hooking portion 37b and a proximal extension section 37a. The label 70 has a form of a square-like sheet having sides 70a along the central axis and sides 70b along the circumferential direction of the outer tube 30, when cut along the central axis of the outer tube 30 and expanded. The side 70a is slightly longer than a half of the overall length of the outer tube 30. The side 70b adjacent to the side 70a is slightly longer than the circumference of the outer tube 30.

The label 70 is made of a transparent film. Approximately the entire area of the film has printing thereon to be opaque. A transparent section 71a having a form of a strip without printing is provided parallel to the side 70b at the portion closer to the distal end than the middle of the label 70. The transparent section 71a divides the label 70 into a distal opaque portion 70c in the distal side and a proximal opaque portion 70d in the proximal side. The background color of the printing on the label 70 is different from the color of the indicator 72 and is, for example, a complementary color of white or red or a color close to such colors. The indicator 72 stands out from such a background color of the label 70. Distances L, M, and N and distance P from the distal surface of the indicating member 72a to the distal edge of a window section 71 are approximately identical. The width of the window section 71 and the width of the side of the indicating member 72a are approximately identical.

Figure 7B:
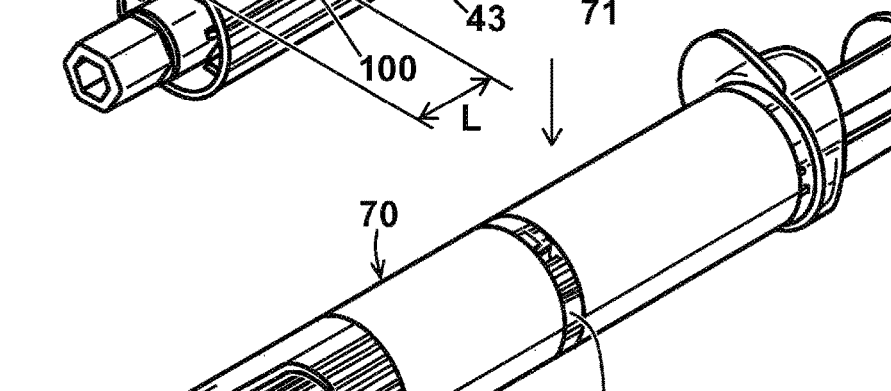

FIG. 7B illustrates the prefilled syringe 1 just before use. The square label 70 is wrapped around and glued on the outer wall of the outer tube 30. The opaque portion of the label 70 conceals the indicator 72. The inside of the outer tube 30 is visible through the window section 71 but the indicator 72 cannot be viewed from outside. The indicating member 72a stays at where the indicator 72 is not visible, before the discharge of the liquid drug 100. With the indicator 72 not being visible, the prefilled syringe 1 is recognized to be unused. A hub 23 is attached to a luer-lock adaptor 42 instead of a cap 21.

Figure 7C:
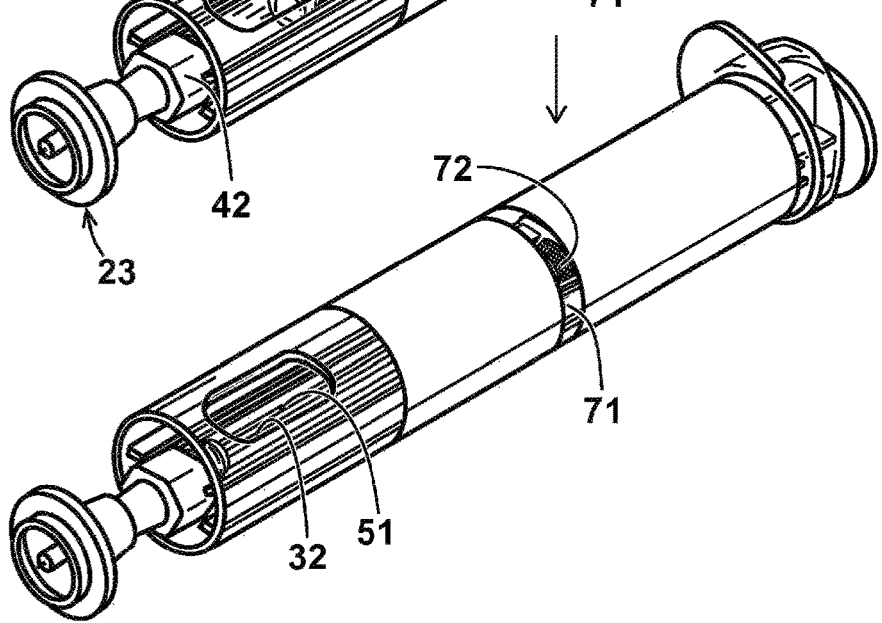

FIG. 7C illustrates the prefilled syringe 1 after used. At approximately the same moment as when the liquid drug 100 is completely discharged, the clicking sound is generated, the shaft portion 51 is exposed through the inspection hole 32, the pressing portion 54 is housed in the proximal extension section 37a, and the indicator 72 is visible through the window section 71, since the distances L, M, N, and P are approximately identical. These indicate that the prefilled syringe 1 has been used.

Figure 8:
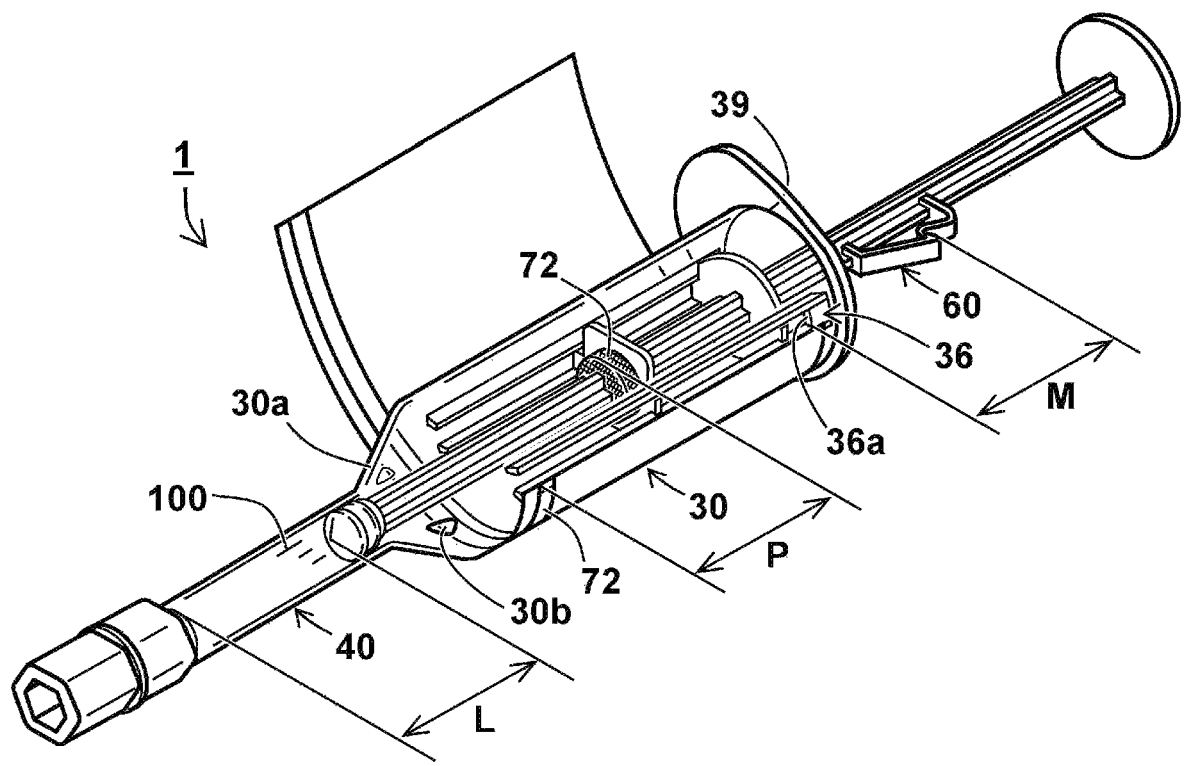
FIG. 8 is a perspective view illustrating another embodiment of the prefilled syringe according to the present invention.

FIG. 8 is a partially exploded perspective view illustrating another embodiment of the prefilled syringe 1. A syringe barrel 10 of the prefilled syringe 1 illustrated in FIG. 8 includes an outer tube 30 and a syringe barrel body 40 integrated together. The outer tube 30 extends from the periphery of an insertion opening 46 of the syringe barrel body 40 toward the opening 39. The outer tube 30 has an inner diameter larger than the inner diameter of the syringe barrel body 40 and an upraised portion 36 provided closer to the proximal end than the insertion opening 46. The outer tube 30 includes a transition section 30a of which diameter expands from the periphery of the insertion opening 46 toward the opening 39. The outer tube 30 is connected to the syringe barrel body 40 via the transition section 30a. Through holes 30b are symmetrically provided about the central axis of the transition section 30a to form steps 36a. The prefilled syringe 1 has approximately identical distances L, M, and P, so that, approximately at the same moment as when the liquid drug 100 is completely discharged, the indicating member 72 is exposed through the window section 71 and the clicker 60 is flipped to generate a clicking sound and a clicking vibration.

Figure 9A:
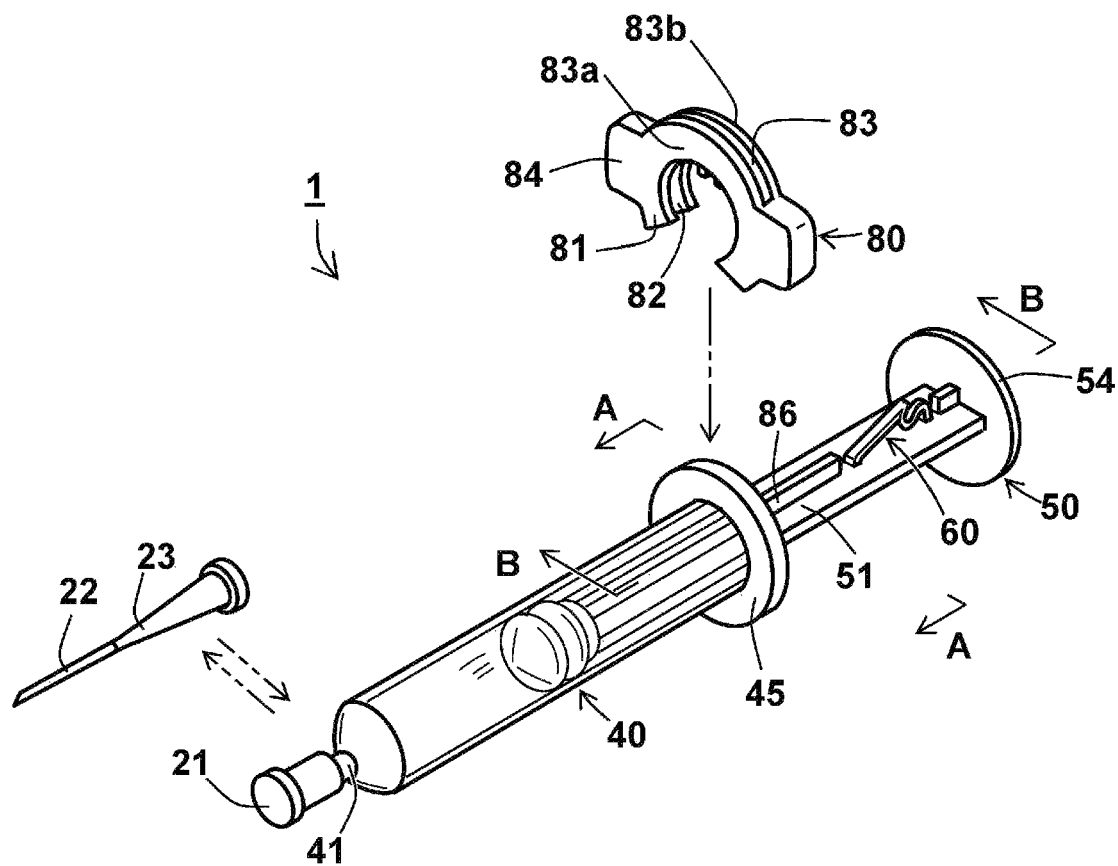
FIG. 9A is a perspective view illustrating another embodiment of the prefilled syringe according to the present invention.

FIG. 9A is a partially exploded perspective view illustrating another embodiment of the prefilled syringe 1. The prefilled syringe 1 is composed of a syringe barrel body 40, a plunger 50, and an adaptor 80 and does not include an outer tube 30. A shaft portion 51 has a crisscross cross section. One of protrusions constituting the crisscross is an engaging protrusion 86. A clicker 60 in line with the engaging protrusion 86 protrudes from the shaft portion 51. The clicker 60 protrudes further than the engaging protrusion 86.

The adaptor 80 has an arc shape and includes a cutout 81 forming an opening of the arc and a finger hooking portion 84 extending in opposite directions. The adaptor 80 includes a recessed portion 82 in the inner wall and a slit 83 penetrating the portion of the adaptor 80 opposite the cutout 81. The adaptor 80 is roughly divided by the slit 83 into two sections which are a front surface section 83a facing the liquid drug discharge portion 41 and a back surface section 83b facing a pressing portion 54. The syringe barrel flange 45 fits into the recessed portion 82 and the slit 83 by widening the cutout 81, deforming the adaptor 80. The adaptor 80 is thus attached to the syringe barrel body 40. The adaptor 80 made of resin has a little flexibility. Although the adaptor 80 receives a force by widening the cutout 81, the adaptor 80 returns by its flexibility to the initial shape when the force is removed after the adaptor 80 has been attached to the syringe barrel flange 45. The syringe barrel flange 45 has a circular outer shape which makes it easy to attach thereto the adaptor 80.

Figure 9B:
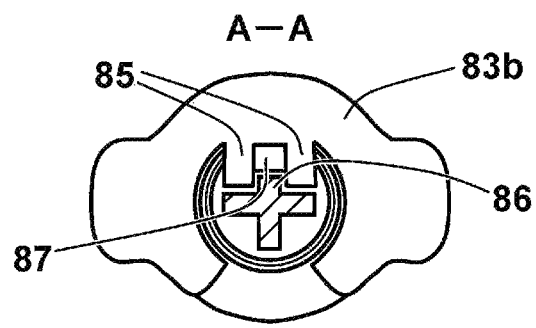
FIG. 9B is a sectional view taken along line A-A in FIG. 9A, illustrating the embodiment of the prefilled syringe according to the present invention.

FIG. 9B illustrates a sectional view taken along line A-A in FIG. 9A. A pair of guiding ribs 85 protrudes from the inner circumference of the back surface section 83b. An engaging protrusion 86 is positioned between a pair of guiding ribs 85. An upraised portion 87 protrudes along on the extending direction of the guiding rib 85 at proximal end.

Figure 9C:
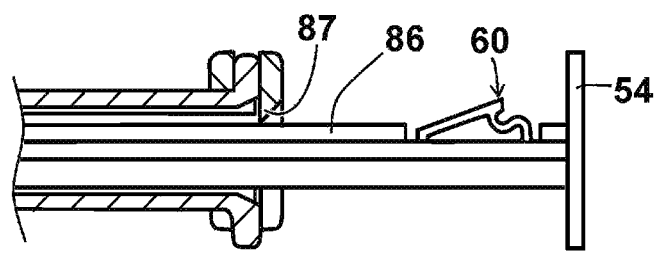
FIG. 9C is a partial sectional view taken along B-B in FIG. 9A, illustrating the embodiment of the prefilled syringe according to the present invention.

FIG. 9C illustrates a sectional view taken along line B-B in FIG. 9A. The pressing portion 54 is pushed toward the liquid drug discharge portion 41 to slide the engaging protrusion 86 along between a pair of guiding ribs 85. The plunger 50 is thus prevented from rotating, and the clicker 60 is smoothly guided to the upraised portion 87. Approximately at the same moment as when the liquid drug 100 is completely discharged, the clicker 60 crosses over the upraised portion 87 to generate a clicking sound and a clicking vibration in the prefilled syringe 1.

In the embodiment, a user places the index finger and the middle finger on the finger hooking portion 84 of the adaptor 80 and pushes the pressing portion 54 with the thumb to administer the liquid drug 100 into a subject person.

The liquid drug 100 stored in the syringe barrel body 40 may be a bio-pharmaceutical such as vaccine for preventing, for example, influenza, tetanus, *Streptococcus pneumoniae*, poliomyelitis, Japanese encephalitis, rubella, measles, yellow fever, Hib, hepatitis, chickenpox, rabies, rotavirus, mumps, or uterine cervix cancer, MQ vaccine, DT vaccine, and DPT vaccine. Examples other than vaccines include: saccharide infusion solutions such as glucose; electrolyte regulating infusion solutions such as sodium chloride and potassium lactate; contrast media; steroids; protease inhibitors; fat emulsions; antibiotics; anticancer agents; heparin calcium; anesthetics; and antibody preparations.

The plunger 50 is usually pushed with a pushing force below 5 N to subcutaneously administer the liquid drug 100 using the prefilled syringe 1. When the plunger 50 is pushed with a pushing force of 5 N or larger, a user pushes the plunger 50 with a pushing force larger than usual. So that a feeling that indicates completion of discharge caused by the gasket 43 abutting the distal end of the inner wall of the syringe barrel body 40 cannot be felt clearly. As a result, the user continues pushing the plunger 50 even after all the liquid drug 100 has been discharged, which results in an unnecessary workload of the user of pushing the plunger 50 with a pushing force greater than a pushing force given during administration. Thus, the prefilled syringe 1 is preferably used when the plunger 50 is to be pushed with a pushing force of 5 N or larger. In particular, the prefilled syringe 1 is preferably used for administering the liquid drug 100 into the intracutaneous tissue stiffer than the subcutaneous tissue, which requires a pushing force of approximately 15 N or larger.

The prefilled syringe 1 may be sterilized by autoclave sterilization or sterilization using any one of ethylene oxide gas, y-ray, and electron ray.

Materials of the cap 21, the hub 23, the outer tube 30, the syringe barrel body 40, the plunger 50, and the adaptor 80 are each selected from a viewpoint of, for example, chemical resistance, barrier properties against gas and bacteria, and safety for living bodies. For example, such materials include: polyolefin resin such as polyethylene, polypropylene, and cyclic polyolefin; polystyrene; polycarbonate; polyester such as polyethylene terephthalate; and polyamide. If sterilization is performed in an autoclave, in particular, a high thermal resistant resin, for example, polypropylene or polycarbonate is preferably used as such material. As the material of the syringe barrel body 40, cyclic olefin homopolymer or cyclic olefin copolymer is preferably used, since such resins have high transparency allowing the liquid drug 100 stored in the tube to be viewed from outside, little interaction with the liquid drug 100, and sufficient stiffness that prevents bending or crushing under firm holding and hard pushing during administration of the liquid drug 100. Components of the prefilled syringe 1 may be formed by injection molding or other methods, such as blow molding and thermal molding.

The material of the gasket 43 is selected from the same view point as described above. For example, thermoplastic elastomer of olefin-base, polyurethane-base, polyester-base, polyamide-base, or styrene-base or rubber materials such as natural rubber, isoprene rubber, butadiene rubber, styrene-butadiene rubber, and silicone rubber may be used.

Materials of the label 70 include: polyolefin such as polyethylene and polypropylene; polyvinyl chloride; polystyrene; polyethylene terephthalate; and paper. For example, the window section 71 may be created by joining together opaque labels, aligned and separated by a distance of the width of the window section 71, with a transparent film. Alternatively, the window section 71 may be created by masking the area on the outer tube 30 where the window section 71 is to be formed, painting the outer circumferential surface of the outer tube 30, and then removing the masking.

INDUSTRIAL APPLICABILITY

A prefilled syringe according to the present invention is used for administering a liquid drug into a patient or a subject person who needs vaccination.

REFERENCE SIGNS LIST 1 prefilled syringe
10 syringe barrel
21 cap
22 injection needle
23 hub
23a annular stabilizer
30 outer tube
30a transition section
30b through hole
31 tube distal portion
32 inspection hole
33 rib
33a tilt-restricting rib
$33a_1$ contact portion
33b support protrusion
33c rotation-restricting rib
33d guiding rib
$33d_1$ distal guiding rib
$33d_2$ proximal guiding rib
$33d_3$ guiding tapered portion
34 restricting protrusion
35 latching claw
35a latching surface
35b latching claw inclined surface
35c latching claw protrusion
36 upraised portion
36a step
36b top
36c upraised portion inclined surface
37 annular protruding portion
37a proximal extension section
37b finger hooking portion
37c taper
38 elastic deformation promoting hole
38a wobble-restricting rib
39 opening
39a cutout
40 syringe barrel body
41 liquid drug discharge portion
42 luer-lock adaptor
43 gasket
44 body portion
45 syringe barrel flange
45a long-axis side surface
45b short-axis side surface
46 insertion opening
50 plunger
51 shaft portion
51a identification portion
52, 53 flange
52a engaging protrusion
53a guide engaging portion
54 pressing portion
60 clicker
60a flexing portion
60b sliding portion
61 distal flexing portion
61a branch-off portion
61b distal inclined portion 62 proximal flexing portion
62a arched section
62b joint portion
63a sliding portion step
63b slider inclined surface
70 label
70a, 70b side
70c distal opaque portion
70d proximal opaque portion
71 window section
71a transparent section
72 indicator
72a indicating member
80 adaptor
81 cutout
82 recessed portion
83 slit
83a front surface section
83b back surface section
84 finger hooking portion
85 guiding rib
86 guiding protrusion
87 upraised portion
100 liquid drug
L, M, N, P, X distance
Y width

The invention claimed is:

1. A prefilled syringe comprising:
a syringe barrel comprising:
   a liquid drug discharge portion on a distal end of the barrel, and
   an opening on a proximal end of the barrel;
a cap detachably attached to the syringe barrel to seal the liquid drug discharge portion;
a gasket located in the syringe barrel;
a plunger comprising:
   a shaft portion inserted in the syringe barrel from the opening, and
   a pressing portion located on a proximal end of the shaft portion and configured to be manually pushed by a user, the plunger being movable toward a distal direction by pushing the pressing portion to slide the gasket toward the liquid drug discharge portion;
a liquid drug stored between the liquid drug discharge portion and the gasket in the syringe barrel, the liquid drug being dischargeable from the liquid drug discharge portion by sliding of the gasket;
an upraised portion located on an inner wall of the syringe barrel between the gasket and the opening and comprising a step protruding approximately perpendicular to a central axis of the syringe barrel; and
a clicker protruding from a side surface of the shaft portion configured to slide against the upraised portion along with a movement of the plunger toward the distal direction and flex inward in a direction approximately perpendicular to a central axis of the shaft portion by sliding up the upraised portion, the clicker being configured to be flipped by crossing over the upraised portion to generate a clicking sound and/or a clicking vibration at approximately a same moment as when the liquid drug is completely discharged,
wherein the clicker comprises:
   a flexing portion branching off from the side surface of the shaft portion and having an inclined section inclined away from the central axis of the shaft portion in a natural state, and
   a sliding portion connected to the flexing portion and configured to slide against the upraised portion,
wherein the flexing portion includes a distal flexing portion that branches off from a side surface of the shaft portion at a location distal of the sliding portion and extends toward the sliding portion, the distal flexing portion including at least part of the inclined section.

2. The prefilled syringe according to claim 1, wherein a height of the step is at least 0.5 mm.

3. The prefilled syringe according to claim 1, wherein a difference between M and L is such that −3.0 mm≤L−M≤3.0 mm, where M is an advancement distance by which the plunger moves until the clicker crosses over the upraised portion and L is a slide distance by which the gasket slides until the liquid drug has completely been discharged.

4. The prefilled syringe according to claim 1, wherein the sliding portion comprises a sliding portion step located at a proximal end of the sliding portion and approximately perpendicular to the central axis of the shaft portion.

5. The prefilled syringe according to claim 1, wherein the flexing portion further comprises a proximal flexing portion that branches off from a side surface of the shaft portion at a location proximal of a location at which the distal flexing portion branches off from the side surface of the shaft portion, the proximal flexing portion being connected to the sliding portion and comprising at least part of the inclined section.

6. The prefilled syringe according to claim 1, wherein the proximal flexing portion branches off from the side surface of the shaft portion at a location proximal of the sliding portion.

7. The prefilled syringe according to claim 1, wherein the upraised portion comprises a slider inclined surface formed such that a distance from the central axis of the syringe barrel gradually decreases toward the distal end of the syringe barrel.

8. The prefilled syringe according to claim 1, wherein the plunger comprises at least one flange that protrudes from the side surface of the shaft portion to contact the inner wall of the syringe barrel, the at least one flange being configured to prevent the plunger from tilting toward the central axis of the syringe barrel.

9. The prefilled syringe according to claim 8, wherein the at least one flange comprises a first flange located distal of the clicker, and a second flange located proximal of the clicker.

10. The prefilled syringe according to claim 1, wherein the syringe barrel comprises:
   a syringe barrel body that comprises the liquid drug discharge portion on the distal end of the syringe barrel body, and an insertion opening opened at the proximal end of the syringe barrel body, the gasket being disposed inside the syringe barrel body; and
   an outer tube that comprises at least a portion extending proximally from a periphery of the insertion opening, the opening provided at the proximal end of the outer tube, and the upraised portion provided at a location proximal of the insertion opening, an inner diameter of the outer tube from the periphery of the insertion opening to the opening being larger than an inner diameter of the syringe barrel body,
   wherein a height of the step is smaller than a half of a difference between the inner diameter of the outer tube and the inner diameter of the syringe barrel body.

11. The prefilled syringe according to claim 10, further comprising:
- a guiding rib or a guiding groove, the guiding rib or guiding groove extending linearly on an inner wall of the outer tube along a central axis of the outer tube, and
- a guide engaging portion located on the shaft portion of the plunger, the guide engaging portion being configured to engage with the guiding rib or the guiding groove to prevent the plunger from rotating and to guide the clicker to the upraised portion.

12. The prefilled syringe according to claim 10, wherein:
the plunger comprises an engaging protrusion located between a portion of the shaft portion to be inserted in the syringe barrel body and the clicker, the engaging protrusion protruding from the shaft portion, and
the plunger and outer tube are configured such that, as the plunger is inserted in the outer tube from the opening, the engaging protrusion crosses over the upraised portion and engages with the step to prevent reuse of the prefilled syringe.

13. The prefilled syringe according to claim 12, wherein:
the syringe barrel body comprises a syringe barrel flange protruding from the periphery of the insertion opening,
the syringe barrel body is located in the outer tube,
the outer tube comprises:
- a support protrusion that protrudes from the inner wall of the outer tube to support a distal surface of the syringe barrel flange, and
- a latching claw protruding from the inner wall of the outer tube at a location circumferentially different from a location the upraised portion, and
the syringe barrel flange is immovably held between the support protrusion and the latching claw.

14. The prefilled syringe according to claim 11, wherein:
the plunger is not fixed to the gasket but a distal end of the plunger makes contact with a proximal end of the gasket to slide the gasket toward the liquid drug discharge portion, and
the clicker engages with the step after crossing over the upraised portion to prevent the plunger from returning to an initial position.

15. A prefilled syringe comprising:
a syringe barrel comprising:
- a liquid drug discharge portion on a distal end of the barrel, and
- an opening on a proximal end of the barrel;
a cap detachably attached to the syringe barrel to seal the liquid drug discharge portion;
a gasket located in the syringe barrel;
a plunger comprising:
- a shaft portion inserted in the syringe barrel from the opening, and
- a pressing portion located on a proximal end of the shaft portion and configured to be manually pushed by a user, the plunger being movable toward a distal direction by pushing the pressing portion to slide the gasket toward the liquid drug discharge portion;
a liquid drug stored between the liquid drug discharge portion and the gasket in the syringe barrel, the liquid drug being dischargeable from the liquid drug discharge portion by sliding of the gasket;
an upraised portion located on an inner wall of the syringe barrel between the gasket and the opening and comprising a step protruding approximately perpendicular to a central axis of the syringe barrel; and
a clicker protruding from a side surface of the shaft portion configured to slide against the upraised portion along with a movement of the plunger toward the distal direction and flex inward in a direction approximately perpendicular to a central axis of the shaft portion by sliding up the upraised portion, the clicker being configured to be flipped by crossing over the upraised portion to generate a clicking sound and/or a clicking vibration at approximately a same moment as when the liquid drug is completely discharged,
wherein the clicker comprises:
- a flexing portion branching off from the side surface of the shaft portion and having a inclined section inclined away from the central axis of the shaft portion in a natural state, and
- a sliding portion connected to the flexing portion and configured to slide against the upraised portion,
wherein the flexing portion includes a plurality of arched sections between a first end of the flexing portion connected to the side surface of the shaft portion and a second end of the flexing portion connected to the sliding portion, each of the plurality of arched sections having a curved and/or bent shape, at least a portion of the plurality of the arched sections including the inclined section.

16. The prefilled syringe according to claim 15, wherein the arched section comprises a first arch at the first end of the flexing portion and a second arch at the second end of the flexing portion, the first arch arching away from the side surface of the shaft portion and the second arch arching toward the side surface of the shaft portion.

17. The prefilled syringe according to claim 15, wherein:
the flexing portion comprises:
- a distal flexing portion that branches off from the side surface of the shaft portion at a location distal of the sliding portion and extends toward the sliding portion, the distal flexing portion including the inclined section, and
- a proximal flexing portion that branches off from the side surface of the shaft portion at a location proximal of the sliding portion, the proximal flexing portion having an arched section and being connected to the sliding portion.

18. The prefilled syringe according to claim 17, wherein the proximal flexing portion is connected to the side surface of the shaft portion at a location proximal of the sliding portion.

19. The prefilled syringe according to claim 17, wherein:
the distal flexing portion comprises a branch-off portion that branches off from the side surface of the shaft portion in a direction perpendicular to the central axis of the shaft portion, and
the inclined section extends from the branch-off portion toward a proximal direction to be connected to the sliding portion and is formed such that a distance from the side surface of the shaft portion gradually increases toward the proximal direction.

20. A prefilled syringe comprising:
a syringe barrel comprising:
- a liquid drug discharge portion on a distal end of the barrel, and
- an opening on a proximal end of the barrel;
a cap detachably attached to the syringe barrel to seal the liquid drug discharge portion;
a gasket located in the syringe barrel;
a plunger comprising:
- a shaft portion inserted in the syringe barrel from the opening, and a pressing portion located on a proximal end of the shaft portion and configured to be manually pushed by a user, the plunger being movable toward a distal direction by pushing the pressing portion to slide the gasket toward the liquid drug discharge portion;

a liquid drug stored between the liquid drug discharge portion and the gasket in the syringe barrel, the liquid drug being dischargeable from the liquid drug discharge portion by sliding of the gasket;

an upraised portion located on an inner wall of the syringe barrel between the gasket and the opening and comprising a step protruding approximately perpendicular to a central axis of the syringe barrel; and a clicker protruding from a side surface of the shaft portion configured to slide against the upraised portion along with a movement of the plunger toward the distal direction and flex inward in a direction approximately perpendicular to a central axis of the shaft portion by sliding up the upraised portion, the clicker being configured to be flipped by crossing over the upraised portion to generate a clicking sound and/or a clicking vibration at approximately a same moment as when the liquid drug is completely discharged, wherein the clicker comprises:

a flexing portion branching off from the side surface of the shaft portion and having a inclined section inclined away from the central axis of the shaft portion in a natural state, and a sliding portion connected to the flexing portion and configured to slide against the upraised portion, wherein the sliding portion comprises a slider inclined surface formed such that a distance from the side surface of the shaft portion gradually decreases toward a distal end of the shaft portion.

21. A method comprising:

using the prefilled syringe according to claim 1 for intracutaneous administration of the liquid drug.

\* \* \* \* \*